(12) United States Patent
Bassler et al.

(10) Patent No.: US 7,894,068 B2
(45) Date of Patent: *Feb. 22, 2011

(54) PRODUCING FILTERS WITH COMBINED TRANSMISSION AND/OR REFLECTION FUNCTIONS

(75) Inventors: Michael Bassler, Menlo Park, CA (US); Peter Kiesel, Palo Alto, CA (US); Markus Beck, Palo Alto, CA (US); Alex Hegyi, Ann Arbor, MI (US); Tobias Buergel, Braunschweig (DE); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 236 days.

This patent is subject to a terminal disclaimer.

(21) Appl. No.: 12/025,394

(22) Filed: Feb. 4, 2008

(65) Prior Publication Data
US 2009/0195852 A1 Aug. 6, 2009

(51) Int. Cl.
*G01N 21/25* (2006.01)
*G01N 21/00* (2006.01)
*G01N 21/55* (2006.01)

(52) U.S. Cl. .................. 356/419; 356/410; 356/432; 356/445

(58) Field of Classification Search .......... 356/410, 356/419, 432, 445
See application file for complete search history.

(56) References Cited

U.S. PATENT DOCUMENTS

| 4,081,277 A | 3/1978 | Brault et al. |
| 4,764,670 A | 8/1988 | Pace et al. |
| 5,151,585 A | 9/1992 | Siebert |
| 5,370,842 A | 12/1994 | Miyazaki et al. |
| 5,445,934 A | 8/1995 | Fodor et al. |
| 5,674,698 A | 10/1997 | Zarling et al. |
| 5,760,900 A | 6/1998 | Ito et al. |
| 5,793,485 A | 8/1998 | Gourley |

(Continued)

FOREIGN PATENT DOCUMENTS

WO WO 99/54730 4/1999

OTHER PUBLICATIONS

Shapiro, H. M., Practical Flow Cytometry, Fourth Edition, Wiley-Liss, 2003, Table of Contents and pp. 49-59, 124-183, 191-197, 345, and 364-366.

(Continued)

*Primary Examiner*—Roy Punnoose
(74) *Attorney, Agent, or Firm*—Stanzione & Kim, LLP

(57) ABSTRACT

A transmissive and/or reflective optical filter can receive input light, which can emanate from objects traveling along paths past the filter, e.g. from biological cells, viruses, colored spots or other markings on documents, and so forth. In response, the filter can provide output light in accordance with a combined transmission function that is approximately equal to a superposition or scaled superposition of a set of simpler transmission functions. The set can include two or more non-uniform transmission functions, a subset of which can be different from each other and positioned relative to each other so that the output light has time variation in accordance with each of the functions in the subset. The subset could include, for example, a random function and a periodic function, a chirp function and a periodic function, or any other suitable combination of two or more simpler functions.

24 Claims, 9 Drawing Sheets

U.S. PATENT DOCUMENTS

| | | | |
|---|---|---|---|
| 5,798,222 A | 8/1998 | Goix | |
| 5,872,655 A | 2/1999 | Seddon et al. | |
| 5,945,676 A | 8/1999 | Khalil et al. | |
| 6,040,578 A | 3/2000 | Malin et al. | |
| 6,429,022 B1 | 8/2002 | Kunz et al. | |
| 6,628,390 B1 * | 9/2003 | Johnson | 356/400 |
| 6,697,542 B2 | 2/2004 | Platzman et al. | |
| 6,816,257 B2 | 11/2004 | Goix | |
| 6,867,420 B2 | 3/2005 | Mathies et al. | |
| 6,906,792 B2 | 6/2005 | Ortyn et al. | |
| 7,195,797 B2 * | 3/2007 | Mearini et al. | 427/248.1 |
| 7,252,360 B2 * | 8/2007 | Hersch et al. | 347/19 |
| 7,274,011 B2 | 9/2007 | Tennant et al. | |
| 7,291,824 B2 | 11/2007 | Kiesel et al. | |
| 7,315,667 B2 | 1/2008 | Schmidt et al. | |
| 7,358,476 B2 | 4/2008 | Kiesel et al. | |
| 7,433,552 B2 | 10/2008 | Kiesel et al. | |
| 7,522,786 B2 | 4/2009 | Kiesel et al. | |
| 7,554,673 B2 | 6/2009 | Kiesel et al. | |
| 7,633,629 B2 | 12/2009 | Kiesel et al. | |
| 7,701,580 B2 | 4/2010 | Bassler et al. | |
| 2003/0235924 A1 | 12/2003 | Adams et al. | |
| 2004/0038386 A1 | 2/2004 | Zesch et al. | |
| 2004/0067167 A1 | 4/2004 | Zhang et al. | |
| 2005/0128479 A1 | 6/2005 | Gilbert et al. | |
| 2006/0274313 A1 | 12/2006 | Gilbert et al. | |
| 2007/0046301 A1 | 3/2007 | Kasapi | |
| 2007/0070347 A1 | 3/2007 | Scherer et al. | |
| 2007/0076210 A1 | 4/2007 | Kiesel et al. | |
| 2007/0145249 A1 | 6/2007 | Kiesel et al. | |
| 2007/0146704 A1 | 6/2007 | Schmidt et al. | |
| 2007/0147189 A1 | 6/2007 | Schmidt et al. | |
| 2007/0147728 A1 | 6/2007 | Schmidt et al. | |
| 2007/0172969 A1 | 7/2007 | Wong et al. | |
| 2008/0013877 A1 | 1/2008 | Schmidt et al. | |
| 2008/0181827 A1 | 7/2008 | Bassler et al. | |
| 2008/0183418 A1 | 7/2008 | Bassler et al. | |
| 2008/0186504 A1 | 8/2008 | Kiesel et al. | |
| 2009/0190121 A1 | 7/2009 | Hegyi et al. | |
| 2009/0194705 A1 | 8/2009 | Kiesel et al. | |
| 2009/0195773 A1 | 8/2009 | Bassler et al. | |
| 2009/0220189 A1 | 9/2009 | Kiesel et al. | |

OTHER PUBLICATIONS

Hoffman, R. A., "Flow Cytometry: Instrumentation, Applications, Future Trends and Limitations", Springer Series on Fluorescence, vol. 6, 2008, pp. 307-342.
Office communication in U.S. Appl. No. 11/702,470, mailed Apr. 25, 2008, 22 pages.
Amendment in U.S. Appl. No. 11/702,470, submitted Jul. 25, 2008, 21 pages.
Office communication in U.S. Appl. No. 11/702,470, mailed Oct. 31, 2008, 22 pages.
Amendment in U.S. Appl. No. 11/702,470, submitted Jan. 30, 2009, 22 pages.
Notice of Allowance and Fee(s) Due in U.S. Appl. No. 11/702,470, mailed Apr. 24, 2009, 15 pages.
Office communication in U.S. Appl. No. 12/022,485, mailed Jan. 16, 2009, 18 pages.
Amendment in U.S. Appl. No. 12/022,485, submitted Apr. 15, 2009, 30 pages.
Amendment in U.S. Appl. No. 12/023,436, submitted Mar. 23, 2009, 22 pages.
Amendment in U.S. Appl. No. 12/024,490, submitted Mar. 24, 2009, 32 pages.
Adams, M.L., Enzelberger, M., Quake, S., and Scherer, A., "Microfluidic integration on detector arrays for absorption and fluorescence micro-spectrometers", Sensors and Actuators, 2003, pp. 25-31.
Office communication in U.S. Appl. No. 12/023,436, mailed Dec. 23, 2008, 15 pages.
Office communication in U.S. Appl. No. 12/024,490, mailed Dec. 24, 2008, 12 pages.
Office communication in U.S. Appl. No. 12/022,485, mailed Jul. 31, 2009, 5 pages.
Response to Restriction Requirement in U.S. Appl. No. 12/022,485, submitted Aug. 27, 2009, 20 pages.
Office communication in U.S. Appl. No. 12/023,436, mailed Jun. 12, 2009, 20 pages.
Amendment in U.S. Appl. No. 12/023,436, submitted Sep. 3, 2009, 29 pages.
Office communication in U.S. Appl. No. 12/024,490, mailed Jul. 22, 2009, 16 pages.
Amendment After Final Rejection in U.S. Appl. No. 12/024,490, submitted Sep. 22, 2009, 28 pages.
"Flow Cytometry", printed from www.wellscenter.iupui.edu/MMIA on Jan. 29, 2008, 4 pages.
Office communication in U.S. Appl. No. 12/023,436, mailed Feb. 5, 2010, 16 pages.
Amendment after Final Rejection in U.S. Appl. No. 12/023,436, submitted Mar. 23, 2010, 24 pages.
Office communication in U.S. Patent Appl. No. 11/698,409, mailed Jun. 11, 2010, 21 pages.
Office Communication in U.S. Appl. No. 12/024,490, mailed Nov. 2, 2009, 14 pages.
Office Communication in U.S. Appl. No. 11/698,409, mailed Nov. 17, 2009, 18 pages.
Office Communication in U.S. Appl. No. 12/023,436, mailed Apr. 16, 2010, 8 pages.
Amendment in U.S. Patent Appl. No. 11/698,409, submitted May 17, 2010, 16 pages.

* cited by examiner

PRODUCING FILTERS WITH COMBINED TRANSMISSION AND/OR REFLECTION FUNCTIONS

The following co-pending applications, each of which is hereby incorporated by reference in its entirety, might be regarded as related to this application: "Sensing Photon Energies Emanating from Channels or Moving Objects", U.S. patent application Ser. No. 11/315,386, now published as U.S. Patent Publication No. 2007/0146704; "Sensing Photon Energies of Optical Signals", U.S. patent application Ser. No. 11/315,926, now published as U.S. Patent Publication No. 2007/0147189; "Sensing Photons from Objects in Channels", U.S. patent application Ser. No. 11/315,992, now published as U.S. Patent Publication No. 2007/0145249; "Obtaining Analyte Information", U.S. patent application Ser. No. 11/316,303, now published as U.S. Patent Publication No. 2007/0148760; "Method and System for Evaluation of Signals Received from Spatially Modulated Excitation and Emission to Accurately Determine Particle Positions and Distances", U.S. patent application Ser. No. 11/698,338; "Method and System Implementing Spatially Modulated Excitation or Emission for Particle Characterization with Enhanced Sensitivity", U.S. patent application Ser. No. 11/698,409; "Producing Sandwich Waveguides", U.S. patent application Ser. No. 11/777,661; "Producing Fluidic Waveguides", U.S. patent application Ser. No. 11/777,712; "Obtaining Information from Time Variation of Sensing Results", U.S. patent application Ser. No. 12/022,485; "Providing Time Variation in Emanating Light", U.S. patent application Ser. No. 12/023,436; and "Transmitting/Reflecting Emanating Light with Time Variation", U.S. patent application Ser. No. 12/024,490.

BACKGROUND OF THE INVENTION

The present invention relates generally to techniques that transmit and/or reflect light emanating from objects. More specifically, techniques can produce and use filters with combined transmission functions.

Various techniques have been proposed for optical filters that receive light emanating from objects. U.S. Pat. No. 6,816,257, for example, describes a laser fluorescent measuring system, used to fluorescent light emitted by a fluorescent substance is imaged onto a photo-multiplier or a multiple detector array. A set of interference filters may be used, such as in front of the photo-multiplier, to filter out resonant light from the fluorescent light or, with multiple detectors, to single out fluorescence emission.

It would be advantageous to have improved techniques for filters, including improved techniques for producing and using filters that receive light emanating from objects.

SUMMARY OF THE INVENTION

The invention provides various exemplary embodiments, including methods and apparatus. In general, the embodiments involve filter components with combined transmission functions.

These and other features and advantages of exemplary embodiments of the invention are described below with reference to the accompanying drawings.

DETAILED DESCRIPTION

Figure 1:
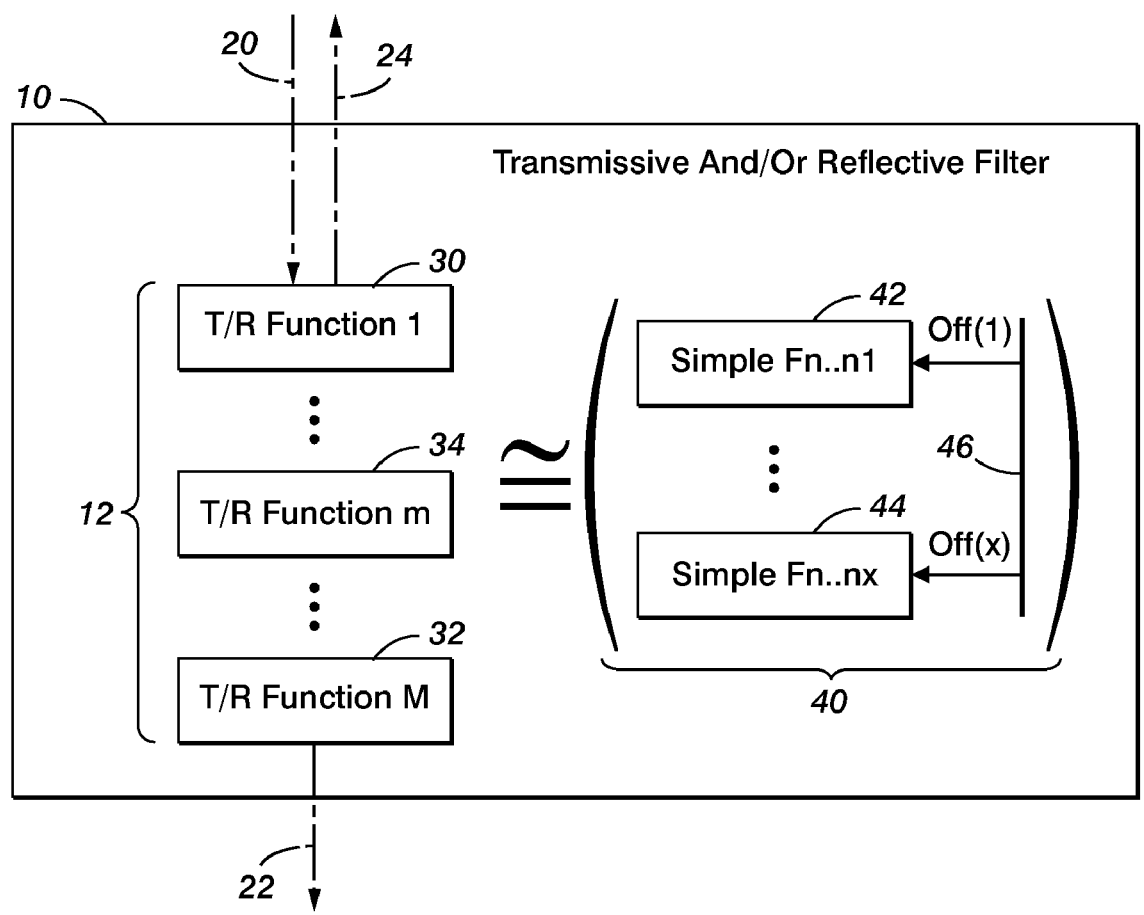
FIG. 1 is a schematic diagram showing features of a filter arrangement in which a filter transmits and/or reflects light, such as light emanating from an object, in accordance with a function in which simpler functions are superimposed.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. Light that can include information is sometimes referred to herein as an "optical signal".

"Photosensing" is sensing of light. A "photosensor" is accordingly an electronic device that performs photosensing. More specifically, if optical signals include information, a photosensor that receives the optical signals may be able to sense the information and provide sensing results that indicate or include the information. A surface at which photosensing occurs is referred to herein as a "photosensitive surface".

The various exemplary implementations described below address problems that arise in obtaining information about a moving object such as a biological cell, a virus, a molecule, or a submolecular complex, such as in flow cytometry. Flow cytometry has become an indispensable tool in clinical diagnostics, such as in diagnosing cancer, AIDS, and infectious diseases during outbreaks, and also in microbiology and other areas. The cost and size of existing cytometers preclude their use in field clinics, water monitoring, agriculture/veterinary diagnostics, and rapidly deployable biothreat detection.

A number of commercially available flow cytometers use multiple excitation sources, each focused on a well-defined location or region separate from the others. Light emitted from each source's region is typically analyzed with a series of beam splitters, filters, and photomultiplier tubes (PMTs) in order to detect and distinguish differently stained cells or cells that concurrently carry multiple dyes. Cells are typically stained in solution with different dyes prior to insertion into a cytometer, and the measurement takes place in a fluidic channel in which cells traverse a detection region, typically at a speed of up to several meters per second. In the detection region, focused laser light (typically with an elliptical focus of 80 µm×40 µm) excites the dyes on the cells. The resulting fluorescent light can be collected by a microscope lens, sorted by band pass filters, and detected by PMTs or avalanche photodiodes (APDs). For each spot excitation, a respective set of filters and detectors is needed, which is costly and leads to bulky devices with strict requirements necessary to maintain optical alignment. Since the detection region is small and objects traverse it rapidly (typical dwell times are around 10 µsec), such flow cytometers have serious signal-to-noise (S/N) ratio issues for weakly fluorescing cells. These issues become more acute if multiple targets must be characterized and distinguished in some way, such as by counting.

A major cost in flow cytometry applied in clinical diagnostics is cost of reagents (e.g. antibodies and conjugated dyes). There are two ways to reduce the amount of consumables: First, one can reduce the required amount of analyte, e.g. by employing microfluidic techniques; and second, one can reduce the amount of consumable per analyte volume. Reducing amounts used would, however, reduce fluorescent intensity. It would be valuable to be able to overcome this constraint with a cost-effective and reliable technique to detect and distinguish weakly emitting cells.

Previous proposals to address these problems have involved spatially modulated single-color excitation to improve S/N ratios and to shift the detection limit toward weaker emitting cells. Spatial resolution can be maintained or improved in comparison with previous flow cytometry techniques, because fluorescing light is spatially modulated over a comparably large detection region; this is helpful because spatial resolution affects maximum detection or count rate of a device. But previously proposed techniques are limited in spectral resolution, whether excitation is performed in a black/white approach or with a single-color interference pattern from a light source.

Some of the problems described above for flow cytometry are similar to problems that arise in scanning images, such as images of documents during printing or copying. For example, in color applications, it is difficult to measure position of colored registration marks to high precision, such as down to 10 µm or less, while also accurately determining color as a function of position. In applications in which a printer applies very small colored marks, such as in a margin of a printed document, and the marks are immediately photosensed and used by the printer to monitor and correct or otherwise adjust its own operation, high levels of spatial and spectral resolution would contribute to accuracy and reliability. In particular, high resolutions are necessary for hyperspectral color sensing applications.

In addressing such problems, some exemplary implementations described below employ filter components with combined transmission functions in which a set of simpler non-uniform transmission functions are superimposed. Such techniques make it possible to concurrently provide multiple transmission functions in a relatively short part of an object's path, so that the object's emanating light is relatively constant across the combined transmission functions. As a result, multiple kinds of information can be concurrently obtained from time variation of emanating light; for example, spectral information such as about color of objects can be obtained at the same time as information about the objects' positions, phases within a pattern, or speeds, making it possible to quickly obtain further information, e.g., color as a function of position. These techniques also allow much greater variation in filter arrangements than would be possible with binary, black/white masks or single color masks. In addition, these techniques can be implemented to maintain higher spatial resolution and to allow higher photon flux on a photosensor.

Time variation of emanating light resulting from such filters may provide sufficient information to make spectral characterization of particles possible. Use of multiple colors may be compatible with particle identification based on native fluorescence; in particular, patterned filter arrangements allow for detection of differences in emission spectra and even the very small differences that occur in native fluorescence spectra might be detectable. It may also enable advanced color monitoring in printing applications by detecting even small differences in the reflection spectra of color spots or other markings while they are moving past interdigitated or otherwise patchworked or patterned filter arrangements.

The term "photon" refers herein to a quantum of light, and the term "photon energy" refers herein to the energy of a photon. Light can be described as having a "photon energy distribution" or, more commonly, a "spectrum", meaning the combination of photon energies that are included in the light; highly monochromatic light, for example, has a photon energy distribution or spectrum with one peak energy value.

To "propagate" light through a region or structure is to transmit or otherwise cause the light to propagate through the region or structure. The light may be referred to as "propagated light" or "propagating light".

Propagating light can often be usefully characterized by direction and speed of propagation, with direction typically illustrated by one or more rays and with speed typically being described relative to the constant c, also referred to as the speed of light in vacuum. Where the speed of light in a medium M is a constant $c_M$ less than c, then M has an index of refraction $n_M = c/c_M$.

Where light changes direction in a way that can be illustrated or approximated as a vertex between an incoming ray and an outgoing ray that are both on one side of a surface, the change may be referred to as a "reflection"; similarly, to "reflect" light is to cause the light to change its direction of propagation approximately at such a surface, referred to herein as a "reflection surface". Similarly, where light changes direction in a way that can be illustrated or approximated as a vertex between an incoming ray and an outgoing ray that are on opposite sides of a surface between two media with different indices of refraction, the change may be referred to as a "refraction"; similarly, to "refract" light is to cause the light to change its direction of propagation approximately at such a surface, referred to herein as a "refraction surface". In many practical applications, both reflection and refraction occur at a surface, which may be referred to herein as a "partially reflecting surface".

Where light propagates at less than c, it may be useful to obtain an "optical distance" of propagation; for any segment of length d in which speed of propagation is constant $\epsilon^* c$, where $\epsilon=1/n_{EFF}\leq 1$ and $n_{EFF}$ is an effective index of refraction for the segment, optical distance $D(\epsilon)=d/\epsilon$. An optical distance may be referred to herein as an "optical thickness", such as where light is propagating through a thickness of material.

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described.

In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange.

Some implementations of filter arrangements described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In the implementations described below, structures, systems, or parts or components of structures or systems may sometimes be referred to as "attached" to each other or to other structures, systems, parts, or components or visa versa, and operations are performed that "attach" structures, systems, or parts or components of structures or systems to each other or to other things or visa versa; the terms "attached", "attach", and related terms refer to any type of connecting that could be performed in the context. One type of attaching is "mounting", which occurs when a first part or component is attached to a second part or component that functions as a support for the first. In contrast, the more generic term "connecting" includes not only "attaching" and "mounting", but also making other types of connections such as electrical connections between or among devices or components of circuitry. A combination of one or more parts connected in any way is sometimes referred to herein as a "structure".

Some of the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

A structure may be described by its operation, such as a "support structure" that can operate as a support as described above; other examples are defined below. In addition, a structure may be characterized by the nature of its parts or the way in which they are connected; for example, a "layered structure" is a structure that includes one or more layers, and the terms "partial structure" and "substructure" refer to structures that are in turn parts of other structures.

In general, sensors, processors, and other such items may be included in a system in which they are operated automatically or partially automatically. As used herein, the term "system" refers to a combination of two or more parts or components that can perform an operation together. A system may be characterized by its operation; for example, an "object distinguishing system" is a system that operates somehow to distinguish objects.

Within a system, device, or other article, components and parts may be referred to in a similar manner. One component of an object distinguishing system, for example, can be described as an "encoding component", in some cases referred to as an "encoding arrangement", in either case meaning that the component or arrangement operates to encode information; similarly, a system can include an "filter component", in some cases referred to as an "filter arrangement", in either case meaning that the component or arrangement operates to perform filtering, as explained in greater detail below; various other components are described below. In addition, a component or part may be identified by characteristics other than its operation.

In FIG. 1, filter component 10 is an optical filter that includes combination 12 of M filter elements. The filter elements in combination 12 transmit and/or reflect light.

The term "optical filter" or simply "filter" refers herein to a light-transmissive or light-reflective part or component that transmits and/or reflects light in accordance with a respective criterion, sometimes referred to herein as a filter's "type". For example, one general category of filters is "band pass filters", referring to types of filters that, across some application's range of photon energies, e.g. a range of wavelengths or frequencies such as the visible range, preferentially transmit and/or reflect light within a subrange, sometimes referred to as a "band"; a band pass filter's type can therefore be specified by specifying the band or subrange of photon energies in which it transmits and/or reflects. A "blocking filter", which does not transmit or reflect any light in an application's range, can be viewed as a band pass filter with a band of zero bandwidth, while a "transparent filter", which transmits and/or reflects all light in an application's range, can be viewed as a band pass filter with a band that includes the entire range.

Filters can be combined and configured in many different ways, and all such combinations and configurations of one or more filters are encompassed herein by the general term "filter arrangement". A filter arrangement can include, for example, one or more "filter components", one or more "filter assemblies", and/or one or more "filter elements"; while the term "filter component" is generic, referring to any component that operates as a filter, the terms "filter assembly" and "filter element" are related and therefore a bit more specific, in that a filter assembly is a filter component that includes one or more filter elements, while a filter element is a filter component that generally does not include other filter elements within it. In general, filter elements and filter assemblies are sometimes also referred to as "masks". Also, the terms "transmit" and "reflect" and related words, as used herein, include each other unless otherwise specified, and terms such as "transmit/reflect" or "transmitting/reflecting" encompass transmission without reflection, reflection without transmission, and concurrent transmission and reflection.

Filter elements of various kinds could be included in filter assemblies, filter components, filter arrangements, and other combinations and configurations of filters, in a wide variety of ways. Within a given configuration of filters, relationships between filters can be described in a number of ways. For example, light can pass through a "sequence" of filters, meaning that specified light passes through the filters in a sequence: If a "radial sequence" of filters is along a path, for example, emanating light can pass through each of the filters in the sequence, beginning with the first and, after passing through each preceding filter, passing through the following filter; of course, light that is blocked by a preceding filter in a radial sequence would not reach its following filter. If a "longitudinal sequence" of filters is along a path, on the other hand, light emanating at each of a sequence of segments on the path passes through a respective filter in the longitudinal sequence.

Several other categories of filters are described below in relation to exemplary implementations, including shadow masks, periodic masks, chirp masks, random masks, and so forth, and various other categories could be identified. As used herein, the term "random" refers to a pattern that is non-periodic over the entire length of a longitudinal sequence of filters; in contrast, a "periodic" filter assembly has at least one pattern that repeats more than once across the assembly's longitudinal length; and "chirp" patterns meet the above definition of random but can, with linearly varying time scaling, meet the above definition of periodic, in effect being a sequence of periods of linearly changing frequency or wavelength. A "shadow mask" is not a band pass filter, but rather an intensity-based filter assembly that, within a photon energy range of interest, transmits/reflects light of all energies, but with different parts of the filter transmitting/reflecting the light at different intensities, such as black and white and/or different gray levels. Any of these types of filter assemblies can be used to obtain "spatially modulated" emanating light, meaning emanating light that varies in time depending on position of an object from which it is emanating.

As used herein, the term "white", in a given implementation, refers to light with a spectrum that approximates maximum intensities across the implementation's full range of photon energies (which could be broad band, a combination of red, green, and blue, or another appropriate combination); the term "black" refers to the opposite of white, i.e. minimum available intensities across the full range, with the ideal being no light and therefore zero intensities. In emanating spectra, for example, light without maximal intensities across the full range as in white may be characterized as having a "gray level", such as one of the gray levels between white and black, or as having a "color", such as if it includes predominantly photon energies in a subrange, e.g. one of the colors in the visible range of wavelengths or in the infrared or ultraviolet ranges, or possibly a combination of such colors. Spectra that are neither black nor white are sometimes referred to herein as "non-binary spectra".

As objects travel along respective paths past component 10, light can emanate from them, such as by emission, scattering (including, e.g. reflection), or transmission, and a portion of the emanating light is received by component 10, as indicated by arrow 20. In general, emanating light includes light within an application's range of photon energies, meaning that techniques as in FIG. 1 can be successfully used in a given application, e.g. flow cytometry, bio-chip readout, any suitable kind of analyte detection, or document scanning even though emanating light might also include photon energies that are outside the application's range and that might not interact with filter component 10 in the same way as light in the application's range.

The term "path" is used herein in the general sense of a series of positions and/or configurations that a moving and/or varying object can have during its motion and/or variation. For generality, a part of a path is sometimes referred to herein as a "segment", which could encompass any continuous series of one or more positions and/or configurations within a path.

The term "object" is used herein in the general sense of any distinguishable thing that can emanate light. In some implementations, light can emanate from an object, whether through emission (e.g. radiation, fluorescence, incandescence, chemoluminescence, bioluminescence, other forms of luminescence, etc.), scattering (e.g. reflection, deflection, diffraction, refraction, etc.), or transmission, and the emanating light can be transmitted and/or reflected through a filter component, such as before being sensed by a photosensor. The light "emanates from" or is simply "from" the object, and may be referred to herein as "emanating light". An object from which light is emanating may be referred to herein as a "light-emanating object".

Examples of objects that could occur in implementations as described below include droplets, small volumes of fluid, single molecules, agglomerated molecules, molecule clusters, cells, viruses, bacteria, lengthy polymers such as DNA or protein chains, submolecular complexes such as tags on DNA or protein chains, microparticles, nanoparticles, beads or other small particles that can bind and carry specific chemicals or other analytes, emulsions, any such type of object in an array such as an array of sample wells, and a distinguishable region of a surface such as a small area of a sheet of paper or other image-bearing medium; a distinguishable region, could, for example, be a colored spot. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that absorb light incident on the droplet, so that the droplet does not reflect or otherwise scatter the absorbed light; in this case, a particle could be an "absorbent component" of a droplet. Or a droplet may include particles that scatter light incident on the droplet in a way that depends on photon energy, so that the droplet scatters the incident light correspondingly; in this case, a particle could be a "scattering component" of a droplet. An analyte (i.e. a chemical species being investigated) in a droplet or other object can act as a fluorescent, absorbent, or scattering component. Analyte that is otherwise homogeneously distributed, for example, can be localized by binding to carrier beads, resulting in a moving object that emanates light or provides other signals in a way that depends on the analyte.

With respect to a light-emanating object, the expressions "characteristic of an object" and "emanating light including information" have related meanings: The term "characteristic" refers to a trait, quality, or property of an object that can be measured and that persists with a given value or within a given range or other subset of possible values while light that "includes information about the characteristic" is emanating from the object. In appropriate implementations, characteristics of an object could include mass, volume, density, cross-section or other shape, chemical composition, position, speed, acceleration, direction of movement, spin axis, directional or angular velocity or momentum, net charge, charge polarity, absorption spectrum, emission spectrum, scattering spectrum, and so forth. Therefore, emanating light "includes" information about a characteristic of an object if information included in the emanating light indicates a value, range, or other measure of the characteristic.

Emanating light or other types of signals can "include information" in many ways, some of which are described below in relation to specific implementations. Various criteria could be used to determine whether emanating light or another type of signal includes specified information, and such criteria can be referred to as "encoding criteria". Some encoding criteria, for example, involve comparison of magnitude of a signal with noise magnitude, e.g. signal-to-noise (S/N) ratios, because S/N ratio can affect whether specified information can be recovered from sensing results obtained by photosensing emanating light. Other types of encoding criteria could be used as appropriate. Where emanating light or another type of signal satisfies an appropriate encoding criterion for specified information, the light or signal may be said to "encode" the information.

In a system in which emanating light can include information about characteristics of objects, an object "travels" or is caused "to travel" if the object has a succession of positions over time with respect to one or more parts or components of the system or one or more patterns or other features of the system's environment such that information about the object's traveling, e.g. about speed or other rate of displacement, can be included in the emanating light or other signals. An object that travels is sometimes also referred to herein as "moving" or as having "motion" or "movement", but an object's traveling may result from any appropriate motion of the object and/or motion of parts or components of the system or patterns or other features of its environment. In other words, motion of an object includes any relative movement between the object and parts or components of a system or patterns or features of the system's environment, such as an encoding or sensing component of the system or a pattern of excitation or of filtering or another environmental pattern or feature.

A moving object's path is treated herein as providing a directional orientation as follows: A direction parallel or approximately parallel to the path is sometimes referred to as a "longitudinal" or "lengthwise" direction, while a direction perpendicular or approximately perpendicular to the path is sometimes referred to as a "radial", "lateral", or "transverse" direction. The lengthwise direction in which the object is moving is sometimes referred to as "forward" or "downstream", while the opposite direction is sometimes referred to as "backward" or "upstream". A radial direction away from the path is "out" or "outward", while a radial direction toward the path is "in" or "inward". Light propagating toward the path may be referred to as "incoming" or "incident", while light propagating away from the path may be referred to as "outgoing". A component or arrangement of components is "along" the path if it is disposed near the path and has some extent in a longitudinal direction. A component or arrangement of components is "around" the path if, in a plane transverse to the path, it intersects multiple radial directions, at least two of which are separated by approximately 180 degrees of arc. A direction that similarly goes around the path is sometimes referred to herein as a "rotation" direction. In general, it should be understood that the above directional orientation is arbitrary and only for ease of description, and that a moving object's path may have any appropriate orientation.

Emanating light that includes information about an object's traveling is sometimes referred to herein as "motion-affected" light, as including "motion-dependent information", or as having "motion-dependent encoding". For example, an object could travel by being conveyed in fluid, such as liquid, gas, or aerosol, along a path in which it emanates light that is transmitted and/or reflected by a filter arrangement to include information about the object's motion, thus becoming motion-affected light; in such a case the object may be referred to as being "carried" by fluid. In another example, an object contained in or otherwise supported by a support structure could travel due to relative scanning movement between the support structure and a filter component or another component such as a photosensor, and it could emanate light that is transmitted and/or reflected so that it becomes motion-affected light.

The input light represented by arrow 20 can be transmitted and/or reflected by component 10, with transmitted light represented by arrow 22 and reflected light represented by arrow 24. Combination 12, which can be a radial sequence, includes M filters elements 30 through 32, each with a respective transmission function, illustratively labeled as "T/R Function 1" through T/R Function M". Filter element 34, the mth in the radial sequence, has a combined transmission function that is approximately equal to the superposition or scaled superposition of set 40 of simpler transmission functions. The set includes at least two simpler non-uniform transmission functions, illustratively x in number and shown as superimposed functions 42 through 44, labeled "Simple Fn . . . n1" through "Simple Fn . . . nx". Each of the simpler transmission functions can be positioned relative to each other for purposes of superposition; these positionings are shown schematically in FIG. 1 as offsets from a reference position represented by line 46, with the offsets being labeled "Off(1)" through "Off(x)". As described below, the offsets could involve various translations, including movements along a direction in which a function vanes or rotation about an axis. As a result of the superposition, with or without scaling, the combined transmission function of element 34 can transmit/reflect emanating light represented by arrow 20 with time variation.

As used herein, the term "transmission function" refers to a function that indicates, for some appropriate position or set of positions, the relationship of output and input light of a light-transmissive and/or light-reflective component such as a filter or filter assembly. A position's transmission function could indicate, for example, ratio of output intensity to input intensity at the position across a range of photon energies, sometimes referred to herein as the transmission function's "transmission spectrum"; a band pass filter, for example, could have approximately the same transmission spectrum at substantially all of its positions. A position could have any of a variety of other kinds of transmission functions, including, for example, an "intensity ratio", indicating the ratio of the position's output intensity to its input intensity, where the same intensity ratio applies to all photon energies across the relevant range; in the simple case in which each position of a filter has either an intensity ratio of zero or one, each position's transmission function could be one of a pair of binary values, such as black/white, ON/OFF, one/zero, or the like.

Further, a band pass filter or other filter element or assembly has a "uniform transmission function" if substantially all its positions have transmission functions that are approximately the same, and such a transmission function may be said to be "approximately uniform" for light transmitted/ reflected through the filter element or assembly. Conversely, a filter element or assembly has a "non-uniform transmission function" if its transmission function is not approximately uniform; examples include periodic, random, and chirp filters as described above.

Transmission functions can, of course, be different from each other in various ways. For example, transmission functions of two positions can differ in "color", meaning that the positions have different transmission spectra; transmission functions with transmission spectra that have the same shape across a relevant range can differ in "intensity", meaning that they have different intensity ratios. Similar terminology can be applied to uniform transmission functions for filter elements, components, or assemblies. Simpler transmission functions that are superimposed to provide a combined transmission function can have different transmission functions; in FIG. 1, a subset that includes at least two of the simpler transmission functions superimposed to provide the combined transmission function of element 34 are non-uniform and different from each other, e.g. functions 42 and 44.

Different transmission functions can also be combined in a number of ways. For example, in a stack or other radial sequence of filters or filter assemblies, transmission functions can be "superimposed", meaning that both transmission functions are applied to light passing through the component, resulting in a combined transmission function in which simpler transmission functions are superimposed. As used herein, a transmission function is "simpler" than a combined transmission function in which it is superimposed with at least one other transmission function, except in cases where the combined transmission function and all of the superimposed transmission functions have the same spectral shape or where the superimposed transmission functions have related shapes that result in uniform loss of detail when superimposed in specific phase relationships; although there are many abstract examples of superpositions that result in uniform loss of detail (e.g. two square waves of the same period and at opposite phase would have a flat line superposition) simplifying superpositions are very unlikely to occur between transmission functions with disparate shapes, such as random and periodic, random and chirped, chirped and periodic, and so forth—some detail might be lost locally in such cases, but most detail is preserved. Simpler transmission functions can be superimposed to obtain a combined transmission function in various ways other than a stack or radial sequence; for example, as described below in relation to some exemplary implementations, a single filter assembly can have a combined transmission function that is "stack-equivalent", meaning that it is approximately equivalent to a stack of filter components with simpler transmission functions. In some cases, including certain types of reflective filters, a stack-equivalent filter assembly can be equivalent to a combination of simpler filters without regard to the order in which they are superimposed, so that it is equivalent to a number of different stacks in which the simpler filters are in different orders. A "scaled superposition" is a superposition that has been somehow scaled after being obtained, such as in ways described below in relation to exemplary implementations; in other words, after obtaining a combined transmission function by superposition of functions 42 through 44, the combined transmission function could be scaled in any appropriate way, such as to modify overall intensity of transmitted/reflected light or to modify spatial resolution.

Because element 34 is within combination 12, input light received by combination 12 from moving objects can be transmitted with time variation. This occurs because of the manner in which the subset of simpler non-uniform functions is superimposed: In other words, functions 42 and 44 and other simpler non-uniform functions are positioned relative to each other so that element 34 provides output light with time variation in accordance with two or more of the functions in the subset. This output light can encode information in various ways, as described below in relation to exemplary implementations.

In contrast, in some exemplary implementations below, a filter assembly can have a longitudinal sequence of band pass filter elements with bands of different colors. As a result, output light from filter elements of different colors will have different intensities, depending on the spectrum of light emanating from an object, so that time variation of the output light encodes information about the emanating light's spectrum, i.e. about the type of the object. In other examples, information about speed or other displacement rate and position can be encoded by longitudinal filter sequences.

Component 10, on the other hand, encodes light differently. Because of the way simpler, non-uniform transmission functions 42 and 44 are superimposed, the transmission function of element 34 encodes information in time variation of transmitted or reflected light, represented by arrows 22 and 24, respectively. If the input light has the same intensity or spectrum while it is emanated by a passing object, the output light from the transmission function of element 34 will be encoded in accordance with both of simpler non-uniform transmission functions 42 and 44. In other words, information in accordance with both of the simpler transmission functions will be concurrently encoded in time variation of the emanating light.

In some exemplary implementations below, for example, a stack or stack-equivalent filter assembly combines a periodic transmission function that can encode information about an object's speed or other displacement rate with a random transmission function that can encode information about an object's spectrum or type or with a chirp transmission function that can encode information about an object's phase, i.e. position within the filter assembly. Emanating light passing through the filter assembly is concurrently encoded with both types of information.

Information about an object, as could be obtained by photosensing output light as in FIG. 1, can be used for a wide variety of purposes. Such information can, for example, be used to distinguish objects. In some applications, such as where the distinguished objects are registration marks in documents or other images, appropriate subsequent operations can be controlled based on the results of distinguishing objects.

Filter component 10 in FIG. 1 could be implemented in many different ways, some of which are described below. In some exemplary implementations below, for example, a filter assembly has a combined transmission function with superimposed simpler, non-uniform transmission functions based on thickness. As a result of these techniques, emanating light will have time variation due to different transmission functions, and the time variation of the emanating light can encode information about the object's spectral interactions such as the spectra in which it and other similar objects absorb, fluoresce, or otherwise interact with light, i.e. about the type of the object.

Figure 2:
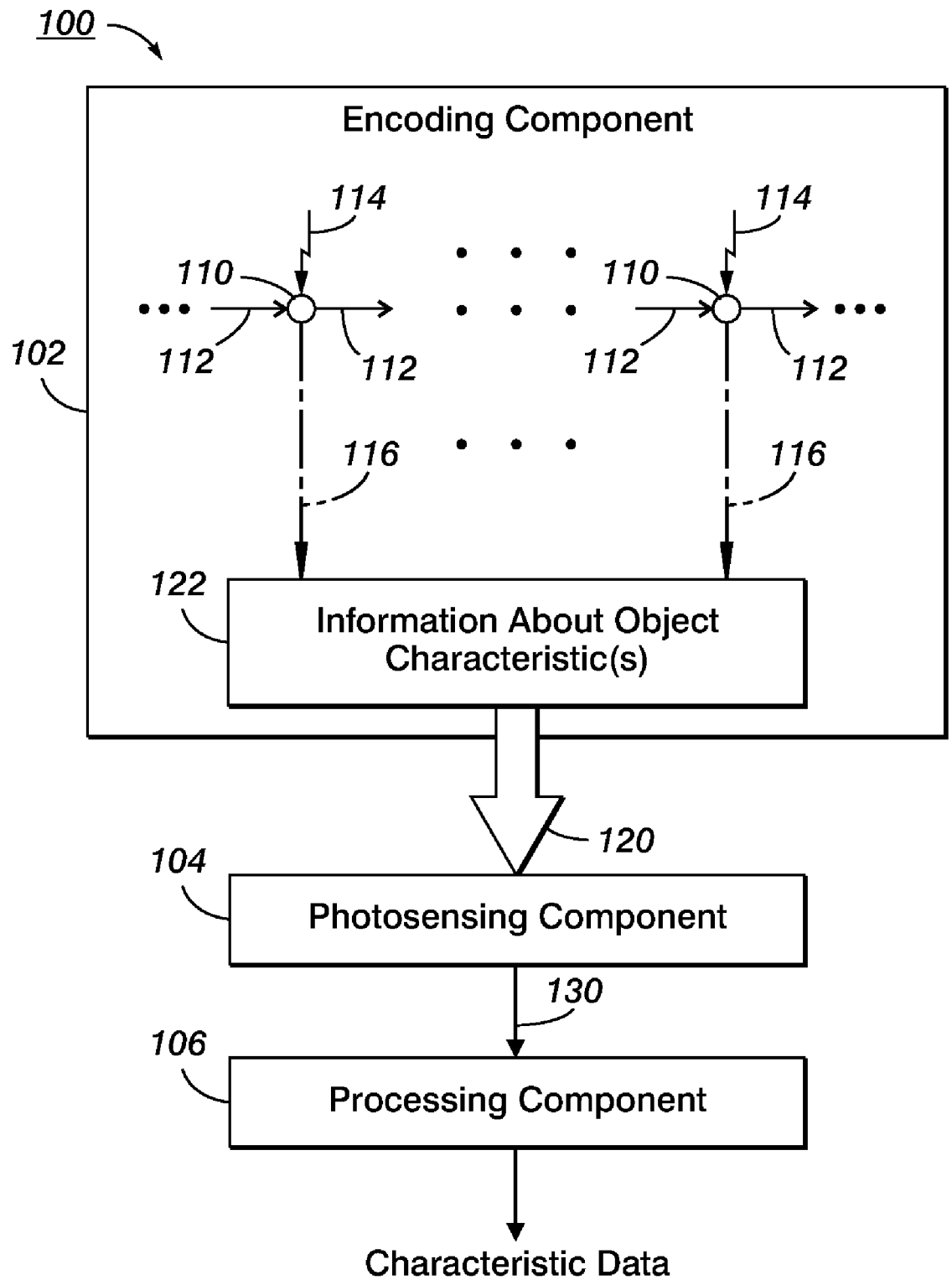
FIG. 2 is a schematic diagram showing components of a system in which light emanating from an object can include information about characteristics of the object.

FIG. 2 schematically illustrates general features of system 100, a system in which light emanating from a moving object can include information about characteristics of the object and in which features described above in relation to FIG. 1 can be implemented. As with other exemplary implementations described below, system 100 involves a combination of parts or components. Encoding component 102 illustratively provides output light that includes information about one or more object characteristics. Photosensing component 104 responds to the output light, providing sensing results such as electrical output signals with information in a form that can be communicated to processing component 106, possibly after conversion to other forms, e.g. for storage, transmission, and processing, such as optical or other electromagnetic signal forms. Processing component 106 can use the sensing results from photosensing component 104 to obtain and/or provide characteristic data indicating information about one or more object characteristics.

Object 110 illustratively travels in a direction indicated by arrows 112, passing through a succession of positions, two of which are illustrated. In some positions, object 110 can receive excitation, illustrated by arrows 114, and, in response, light as illustrated by arrows 116 can emanate, such as from fluorescence of a dye or other "tag" attached to object 110 or from native fluorescence or autofluorescence of object 110 itself, e.g. due to ultraviolet light or other excitation of intrinsic cell material or other material in object 110; except as otherwise noted, however, implementations described herein can additionally or alternatively employ chemofluorescence, biofluorescence, absorption, scattering, or other phenomena that do not require concurrent excitation. More generally, excitation could take any appropriate form and is not limited to illumination, and excitation and emanation need not be concurrent or otherwise coincident, but could have any appropriate relationship in space and time. Additional description of excitation techniques is set forth in co-pending U.S. patent application Ser. No. 12/023,436, entitled "Producing Time Variation in Emanating Light", incorporated herein by reference in its entirety.

Arrow 120 represents output light from encoding component 102. Box 122 between arrows 116 and arrow 120 illustrates that information about one or more characteristics of object 110 is included in the output light. As described below in relation to exemplary implementations, this information can be encoded in a variety of ways, including, for example, patterning excitation and/or patterning emanating light to obtain encoded output light represented by arrow 120.

Arrow 120 points to photosensing component 104, indicating that at least part of the encoded output light is illustratively sensed by component 104 to obtain sensing results. Based on the sensing results, component 104 provides electrical output signals represented by arrow 130. The electrical output signals can also include at least some of the information about object characteristics from box 120. As a result, processing component 106 can, in response to the electrical output signals, obtain and/or provide characteristic data indicating information about object characteristics.

Figure 3:
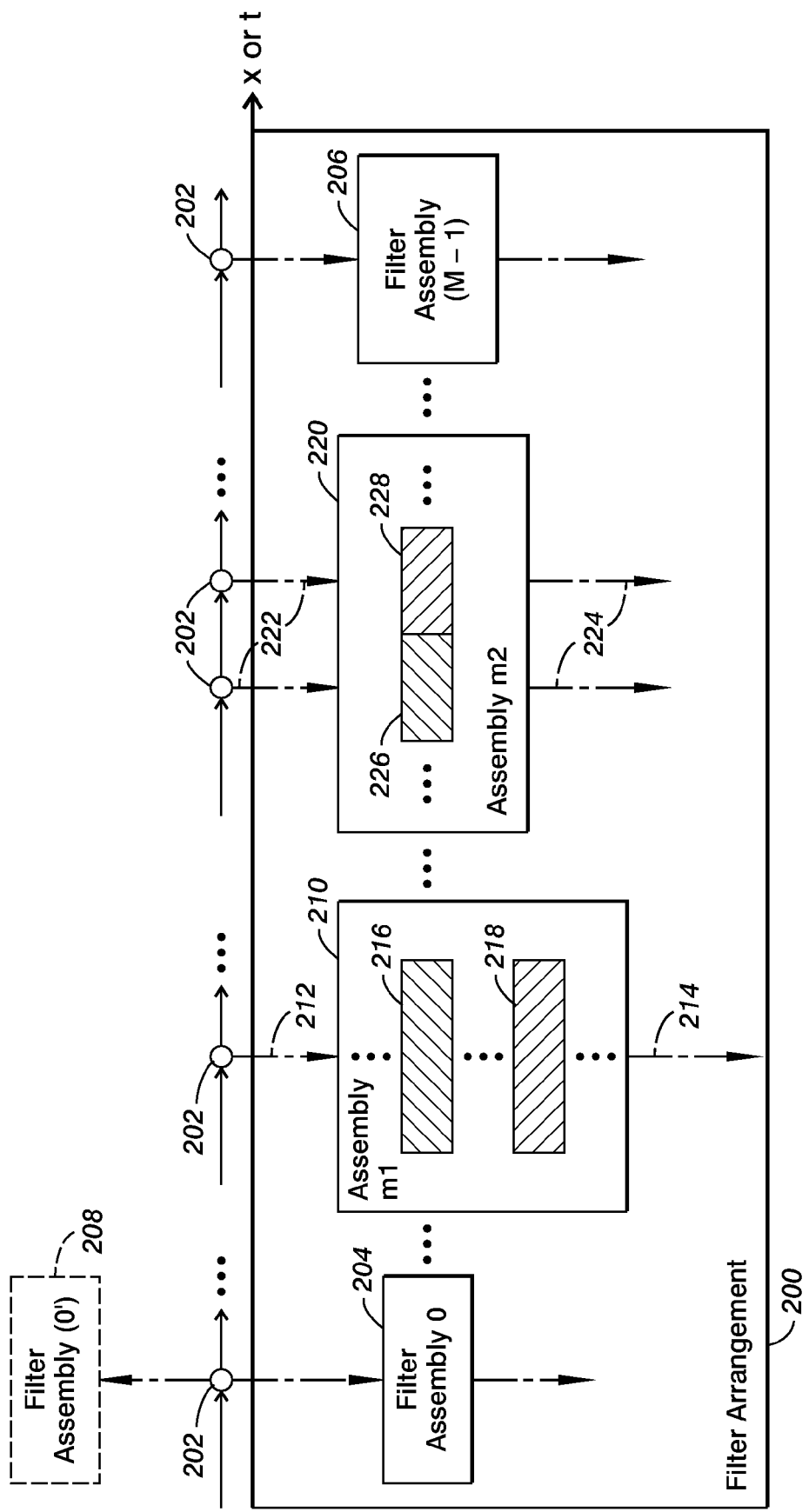
FIG. 3 is a schematic diagram of a filter arrangement in an encoding component as in FIG. 2.

Each of components 102, 104, and 106 in FIG. 2 could be implemented in a wide variety of different ways. FIG. 3 illustrates general features of implementations of encoding component 102 that involve a filter arrangement along a path traveled by a moving object.

In FIG. 3, filter arrangement 200 is along a path traveled by moving object 202 as it emanates light within an encoding component such as component 102 in FIG. 2. Filter arrangement 200 includes a combination of one or more filter assemblies along the path traveled by object 202. As suggested by the one-dimensional coordinate axis labeled "x OR t", the path can be treated either as extending in space, such as along an x-direction, or as occurring over time, t; unless otherwise indicated hereafter in relation to a specific exemplary implementation, the x-direction refers to an object's path and therefore might not in some cases follow a straight line relative to the environment. Although the speed or other rate of displacement of object 202 may vary as it travels along the path, information about its speed or other rate of displacement can be sufficient to allow an approximate mapping between its x-direction positions and times t; more generally, mapping between an object's x-direction positions and times t can be based on any suitable system, such as with trigger detection techniques as described in U.S. Patent Application Publication No. 2007/0145249, entitled "Sensing Photons from Objects in Channels", and co-pending U.S. patent application Ser. No. 12/023,436, entitled "Producing Time Variation in Emanating Light", each incorporated herein by reference in its entirety, or from other techniques, including obtaining information such as a trigger signal from an object's encoded signal.

Although filter assemblies could be positioned in any appropriate way along a path, the exemplary implementations described below generally involve arrangements of filter assemblies along the x OR t axis, and FIG. 3 shows several exemplary cross sections of filters within a sequence of M filter assemblies 204 through 206, with each cross section being taken parallel to the x OR t axis and with assembly 204 labeled "0" and assembly 206 labeled "(M-1)". Filter assemblies need not, however, be arranged on only one side of the path as shown, but rather could be positioned at any suitable positions around the path, depending on directional intensity variations of emanating light. Also, two or more filter assemblies could be at the same position or in overlapping position ranges along the x OR t axis, but displaced in a rotation direction; a configuration of filter assemblies that are sufficiently displaced in a rotation direction so that they are around the path is suggested by box dashed-line box 208 in FIG. 3, representing a possible position of another filter assembly labeled "(0')" in arrangement 200, on the opposite side of the path traveled by object 202 from filter assembly 204.

Filter assembly 210, labeled "m1", illustratively includes a radial sequence of filters through which light emanating from object 202, represented by arrow 212, can pass, with the output light from filter assembly 210 being represented by arrow 214. Filter assembly 210 could include any appropriate number of filters, with filters 216 and 218 being shown in FIG. 3. Furthermore, filter assembly 210 could include a filter that is equivalent to superimposed filters with simpler transmission functions as described below in relation to exemplary implementations.

The overall sequence of filter assemblies 204 through 206 illustrates a longitudinal sequence. Further, filter assembly 220 includes a longitudinal sequence of filters through which light emanating from object 202, represented by arrows 222, can pass, with the output light from filter assembly 220 being represented by arrows 224. Filter assembly 220 could include any appropriate number of filters in any appropriate longitudinal sequence, with adjacent filters 226 and 228 being shown in FIG. 3. Each of filters 226 and 228 could, for example, be a band pass filter, with the bands of filters 226 and 228 being sufficiently different to provide useful information about an emanation spectrum of object 202. Such a filter assembly is sometimes referred to herein as a "spatially patterned filter", because the filters it includes can be treated collectively as a single filter that has a pattern that varies as a function of position. Several examples of spatially patterned filters are described below in relation to exemplary implementations, and one or both of filters 216 and 218 in assembly 210 could also be implemented as a spatially patterned filter.

In the specific example of filter assembly 220, output light per arrows 224 can include encoded information from filters 226 and 228, and the encoded information can be recovered by photosensing the output light and performing appropriate operations on the sensing results. In general, filters 226 and 228 and other filters in filter assembly 220 can have any suitable lengths in the x OR t direction that allow recovery of the encoded information by photosensing and signal processing, including lengths smaller than the apparent extent of object 202 in the x OR t direction that may result in some loss of resolution analogous to blurriness or smearing. As described in relation to some exemplary implementations below, however, each of filters 226 and 228 can have length in the x OR t direction greater than or equal to an apparent extent of object 202 in the x OR t direction, while the lengths of filters 226 and 228 (and other filters in assembly 220) can be sufficiently small that characteristics of object 202 indicated by emanating light do not change while object 202 is traveling past assembly 220. In some specific implementations, filters 226 and 228 have parallel sides extending in a direction transverse to the path, and an assembly of such filters is sometimes referred to herein as a "striped filter" in which each stripe can be specified by filter type and its length (or width) in the lengthwise direction.

In the specific example of filter assembly 220, output light per arrows 224 can include encoded information from filters 226 and 228, and the encoded information can be recovered by photosensing the output light and performing appropriate operations on the sensing results. Several techniques for obtaining encoded information are described in co-pending U.S. patent application Ser. No. 12/022,485, entitled "Obtaining Information From Time Variation of Sensing Results", and Ser. No. 12/024,490, entitled "Transmitting/Reflecting Emanating Light with Time Variation", both incorporated herein by reference.

In general, filters 226 and 228 and other filters in filter assembly 220 can have any suitable lengths in the x OR t direction that allow recovery of the encoded information by photosensing and signal processing, including lengths smaller than the apparent extent of object 202 in the x OR t direction that may result in some loss of resolution analogous to blurriness or smearing. As described in relation to some exemplary implementations below, however, each of filters 226 and 228 can have length in the x OR t direction greater than or equal to an apparent extent of object 202 in the x OR t direction, while the lengths of filters 226 and 228 (and other filters in assembly 220) can be sufficiently small that characteristics of object 202 indicated by emanating light do not change while object 202 is traveling past assembly 220. In some specific implementations, filters 226 and 228 have parallel sides extending in a direction transverse to the path, and an assembly of such filters is sometimes referred to herein as a "striped filter" in which each stripe can be specified by filter type and its length (or width) in the lengthwise direction.

Filter arrangements similar to those shown in FIG. 3 may find application not only in fluidic implementations as described below but also in implementations in which objects in an array move relative to other components due, for example, to scanning movement. One such area of application is in image scanning, such as with scanning sheets of paper or other media that can bear images. In particular, object 202 could be a colored spot on a sheet of paper or other medium, and a filter arrangement could be used to obtain information about small differences in color of light emanating from object 202, e.g. color of reflected light in response to broadband illumination. Such information could be used to obtain position and/or color of object 202; for example, if object 202 is a registration mark with a color unique to registration marks, its color could be accurately distinguished from spots of other colors using techniques as described herein and its position could be obtained with sufficient accuracy to allow registration of the sheet, whether for image sensing or for printing or another operation on the sheet. Very high accuracy sensing of color is sometimes referred to as "hyperspectral color sensing".

Figure 4:
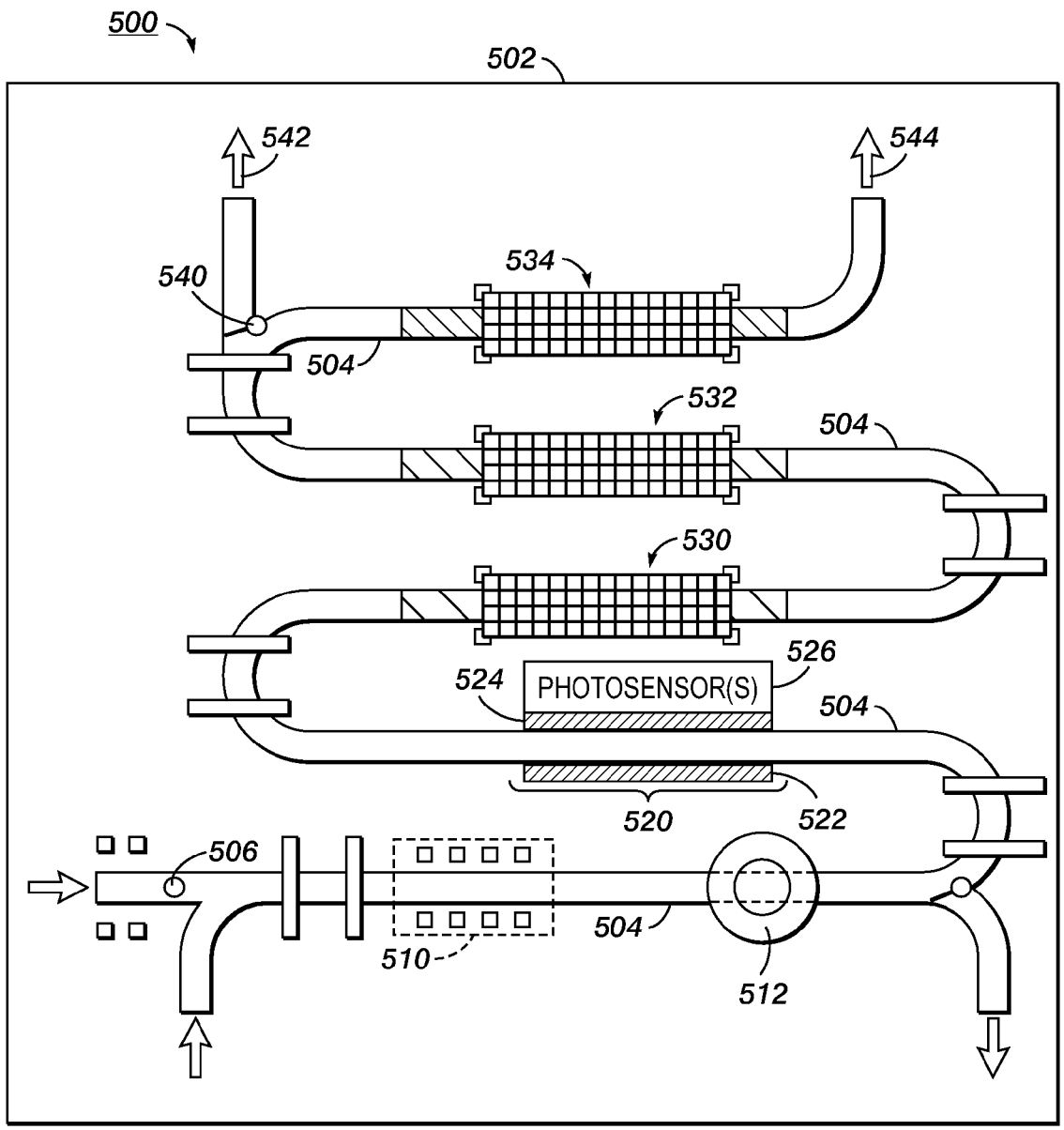
FIG. 4 is a schematic diagram of an analyzer in a fluidic structure, where the analyzer can include components as in FIG. 2.

FIG. 4 illustrates analyzer 500 on support structure 502, a fluidic structure. Defined in support structure 502 is serpentine channel 504 through which object 506 can travel, carried by fluid such as liquid, gas, or aerosol or moved in some other appropriate way. Object 506 can, for example, be a biological cell or another object of any of the types mentioned above.

The manner in which object 506 enters channel 504 and is carried by fluid can be the same as described in U.S. Patent Application Publication Nos. 2007/0145249, entitled "Sensing Photons from Objects in Channels", and 2007/0146704, entitled "Sensing Photons Energies Emanating from Channels or Moving Objects", each of which is incorporated herein by reference in its entirety. As explained there, object 506 can be carried through channel 504 by operation of propulsion components and can be purged or otherwise caused to exit, together with fluid that is carrying it, from one of several outlets, such as through toggling of valves. While in channel 504, object 506 can travel through a series of sensing components, each of which can obtain information about object 506.

The first two sensing components after object 506 enters channel 504 are illustratively Coulter counter 510, an electrically based particle size detector, and Mie scatter sensor 512, also a particle size detector. Information about size of object 506 from Coulter counter 510 and Mie scatter sensor 512 can be used in obtaining information about its other characteristics.

The next sensing component along channel 504 is emanating light encoder/photosensor 520, shown schematically in a cross-sectional view along an axis similar to the x OR t axis in FIG. 3, although it would typically be implemented instead with components above and below channel 504, similarly to other sensing components described below. The schematic illustration of encoder/photosensor 520 includes excitation/displacement component 522, filter component 524, and photosensing component 526, all of which might be implemented in a variety of ways, including some of those described above and below.

After passing through encoder/photosensor 520, object 506 could be characterized without obtaining further information, or, as in the illustrated implementation, object 506 can continue through subsequent sensing components, illustratively including components 530, 532, and 534. These could, for example, include first and second fluorescence sensing components and a Raman scatter sensing component. Information obtained from any combination of the sensing components can be used to distinguish between types of objects, such as different types of biological cells, or to distinguish objects from environment or background. Based on such a distinction, valve 540 at a bifurcation junction can be toggled between two positions, with object 506 exiting as indicating by arrow 542 if valve 540 is in one position and exiting as indicated by arrow 544 if valve 540 is in another position.

The fluidic implementation in FIG. 4 is merely illustrative of a wide variety of implementations of the techniques described herein. For example, any appropriate fluidic or nonfluidic techniques could be used with a wide variety of different types of objects and various types of relative motion to gather various types of information about object characteristics.

Figure 5:
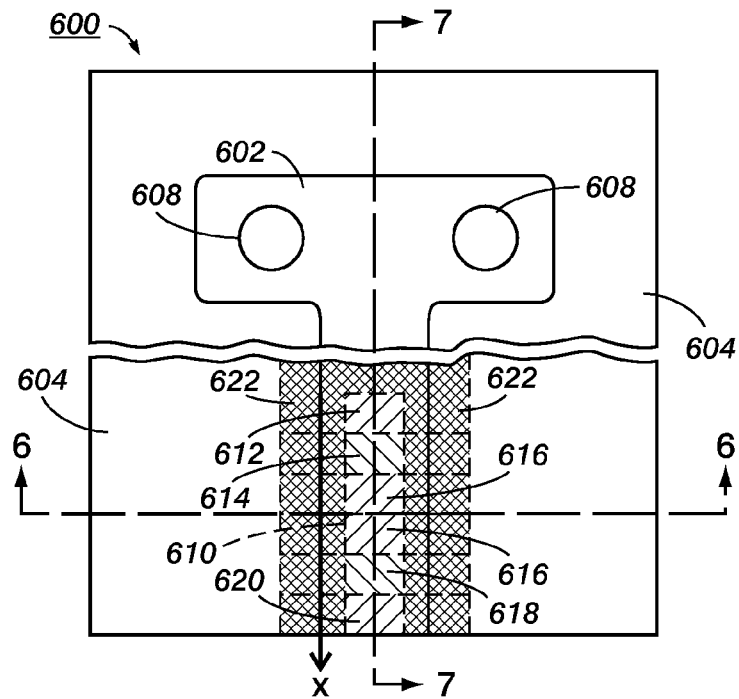
FIG. 5 is a top view of an article that can include a filter arrangement and that can be included in an encoding component as in FIG. 2.

FIG. 5 illustrates an example of article 600 with components that could be operated similarly to encoder/photosensor 520 in FIG. 4. Some features of article 600 can be understood from description in co-pending U.S. patent application Ser. No. 11/777,712, entitled "Producing Fluidic Waveguides", incorporated herein by reference in its entirety. For example, article 600 includes a "fluidic structure", used herein to refer to a structure that depends for its operation on fluid positioning or fluid flow, such as, for liquids or gases, in response to pressure or, for liquids, as a result of surface tension effects, in general, the term "fluid" is used herein to encompass all media that can flow, including liquids, gases, aerosols, and so forth. The related term "channel" refers herein to any tube or other enclosed passage within a fluidic structure through which fluid flows during operation. A channel is therefore an example of a "fluidic region", used herein to refer to a region that can contain fluid. An operation "positions" fluid in a channel if it changes the fluid's position in any way that leaves the fluid in the channel.

A channel or portion of a channel through which objects can travel along paths are treated herein as having the directional orientation described above in relation to a path. In addition, a "cross section" lies in a plane perpendicular to a direction in which a local net flow of fluid through the channel or portion can occur; a direction in which a cross section extends can be referred to as a "transverse direction" or a "lateral direction." A channel or portion with approximately uniform cross section and substantially linear longitudinal direction can be referred to as "straight", and the channels and portions described herein are generally straight unless otherwise indicated.

In order to contain fluid, a channel or other fluidic region is typically "bounded", meaning that surfaces or surface areas bound it on at least some sides. A "boundary" of a channel or portion is the surface or combination of surfaces within which fluid contained in the channel is confined. A "port" is an opening that extends through the boundary of a channel or portion such that fluid can enter or exit through the port; in general, a port is relatively small compared to the length of the channel or portion, and the boundary is treated as extending across the port as if the port did not exist.

As described below, article 600 can include two light-transmissive components, and FIG. 5 shows article 600 in a top view through one light-transmissive component. In this view, the inner region between the light-transmissive components includes two main portions, channel portion 602 that can contain fluid and non-channel portion 604 that surrounds channel portion 602; channel portion 602 is illustratively shaped like a "T", but could instead have an L-shape or any other suitable shape, including a serpentine shape as in FIG. 4. Ports 608 are openings through one of the light-transmissive components, allowing entry and exit of fluid into and out of channel portion 602.

FIG. 5 also shows filter assembly 610 in dashed outline. Filter assembly 610 illustratively includes a spatially patterned filter with a longitudinal sequence of band pass filters that includes filters 612, 614, 616, 618, and 620 and also includes a stack-equivalent filter as described below. Filters 612, 616, and 620 are illustratively cross-hatched similarly to each other to indicate that they have the same or approximately the same band, while filters 614 and 618 are also cross-hatched similarly to each other, illustrating that they also have the same or approximately the same band, a band that is different than that of filters 612, 616, and 620. In other words, filter assembly 610 includes a striped filter in which each of filters 612 through 620 can be specified by the band that it passes and its length in the x-direction in FIG. 5.

Surrounding filter assembly 610, blocking material 622 is structured and positioned to provide an aperture. Blocking material 622 can, for example, be a material with approximately zero light transmission that prevents scattering and reflection of light, also preventing light entering filter assembly 610 from nearby fluorescing objects. Blocking material 622 can be produced during the same operation that produces filters 612 through 620 and can in effect be part of filter assembly 610.

Figure 6:
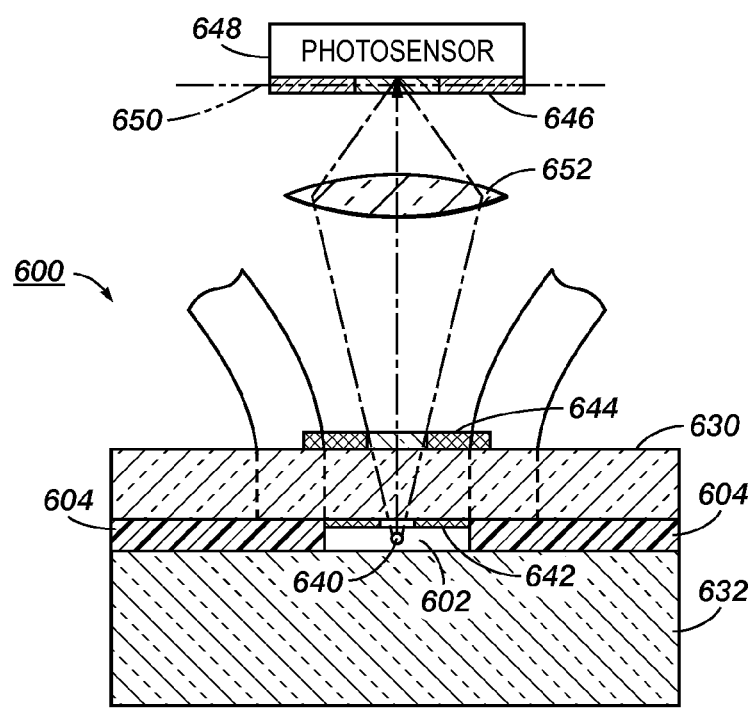
FIG. 6 is a cross-sectional view of an implementation of an article similar to that in FIG. 5, taken along the line 6-6.

The cross section in FIG. 6 shows how light-transmissive components 630 and 632 are separated by material in non-channel portion 604. For example, components 630 and 632 can each include quartz or another suitable material such as glass or acrylic with an appropriate thickness; in a successful implementation, for example, component 630 has a thickness of approximately 0.3 mm, while component 632 has a thickness of approximately 1.0 mm or less; depending on the application, on stability of materials used, and size of objects being characterized, suitable thicknesses might range from a few millimeters down to 0.1 mm or even less. The optimum distance between them is determined primarily by the size of objects being characterized. For biological cells with typical dimensions of 10 μm, for example, the distance can be approximately 20 to 50 μm, maintained by material in non-channel portion 604, which could, for example, be a suitable photoresist material such as SU-8 or another polymer material. Alternatively, a wall (not shown) could be formed around channel portion 602, and non-channel portion 604 could then be filled with epoxy material that seals a lateral boundary around channel portion 602. Various other techniques could be used to produce a similar fluidic structure, including hot embossing, nano-imprinting, or injection molding, and channel portion 602 can have appropriate dimensions, such as for waveguiding as described in co-pending U.S. patent application Ser. No. 11/777,712, entitled "Producing Fluidic Waveguides", incorporated herein by reference in its entirety.

FIG. 6 also shows object 640 from which light is illustratively emanating upward, as illustrated by an emission cone. Although the emission cone is illustratively shown as a single cone, the actual emission cone would depend on angles of total internal reflection at surfaces through which emanating light is transmitted in article 600. FIG. 6 illustrates three alternative filter assembly positions, with filter assembly 642 facing channel portion 602, on the lower surface of component 630; with filter assembly 644 being outside of channel 602 on the upper surface of component 630; and with filter assembly 646 being spaced apart from the upper surface of component 630, adjacent photosensor 648, which could, as in other implementations, be a single, large area photosensor (such as a photo-diode, an avalanche photo-diode (APD), or a photo-multiplier tube (PMT)), or an appropriate array of photosensing cells whose sensed quantities can be combined to obtain a single photosensed quantity, such as an intensity value for a sensing period. As suggested in FIG. 6, the emission cone from object 640 is imaged onto image plane 650 extending through filter assembly 646 by optical component 652, illustratively shown as a single lens, but which could be any suitable lens, lens system, or other optical component, some examples of which are described in co-pending U.S. patent application Ser. No. 11/698,409, entitled "Method and System Implementing Spatially Modulated Excitation or Emission for Particle Characterization with Enhanced Sensitivity", incorporated herein by reference in its entirety.

The emission cone for filter assembly 642 includes the range of angles of incident light that are not totally reflected by the surface of assembly 64. Similarly, the emission cone of filter assembly 644 is determined by the range of angles within which emanating light is not subject to total internal reflection at the surface between component 630 and assembly 644. The emission cone for filter assembly 646 is similar to that for filter assembly 644, but can occupy a smaller area on filter assembly 646 due to the effect of optical element 652.

In one illustrative example, channel portion 602 contains water with an index of refraction n=1.33, and object 640 has a diameter d=7 µm, which would be typical for certain biological cells, e.g. T-lymphocytes. Channel portion 602 has a height between components 630 and 632 of 30 µm and its distance from the lower surface of filter assembly 642 is approximately h=15 µm. Component 630 is acrylic with an index of refraction n=1.48, surrounded by air with an index of refraction n=1. If filter assembly 642 were absent, the escape angle from channel portion 602 to component 630 would be α(escape)=48.75°, which would determine the size of the emission cone in which light from object 640 can leave channel portion 602. The angle of total internal reflection at the upper surface of component 630, on the other hand, can be obtained as α(TIR)=42.51°, which determines the size of the emission cone for light that leaves component 630. The diameter of a disk illuminated by object 640 at the water-acrylic interface can be obtained from D=d+2*h*tan (α(escape))= (7+(2*17.1)) µm=41.2 µm, where 17.1 µm is the radius of the maximum emission cone that can pass through component 630 without total internal reflection. The "minimum feature size" ("MFS") for a pattern suitable to detect object 640 at the water-acrylic interface would be equal to D or approximately 40 µm; in general, MFS can be defined for a mask along the path of an emanating particle as the extent in the path's longitudinal direction of the mask's smallest uniform feature (i.e. the smallest transmitting filter element or the smallest blocking filter element, whichever is smaller).

Where photosensor 648 is implemented with a numerical aperture that makes the emission cone smaller, filter assembly 642 can accordingly have a slightly smaller MFS than calculated as above; similarly, in some acrylic implementations of component 630, some light typically leaves component 630 at an angle slightly higher than α(TIR), which could also allow a slightly smaller MFS. In general, however, the MFS of filter assembly 642, if too small, results in passage of light from an object's emission cone around both sides of a feature in assembly 642, so that the time-varying signal of a photosensor, while containing some information, may not accurately indicate information about displacement of the object as it travels along a path past filter assembly 642. Similar considerations apply to filter assemblies 644 and 646, with the MFS of filter assembly 644 necessarily being significantly larger than that of filter assembly 642, but with the MFS of filter assembly 646 possibly being intermediate between those of assemblies 642 and 644, depending on the precision of optical component 652. In implementations without optical components, photosensor 648 could be slightly larger due to spreading of emanating light. For a biological cell on the order of 10 µm, a typical MFS would be in the range of 10-20 µm. The channel width might be an order of magnitude larger, while the channel length might be two orders of magnitude larger, and the width of the filter assembly would depend on the channel width. For example, assembly 642 might be 100 µm wide and approximately 1.0 mm long. At the time of manufacture, a calibration operation could be performed using objects that are, for example, tiny beads with known fluorescence spectra; light emanating from such beads could be measured and used to obtain calibration values necessary to adjust measured values to obtain known intensities for such objects.

Figure 7:
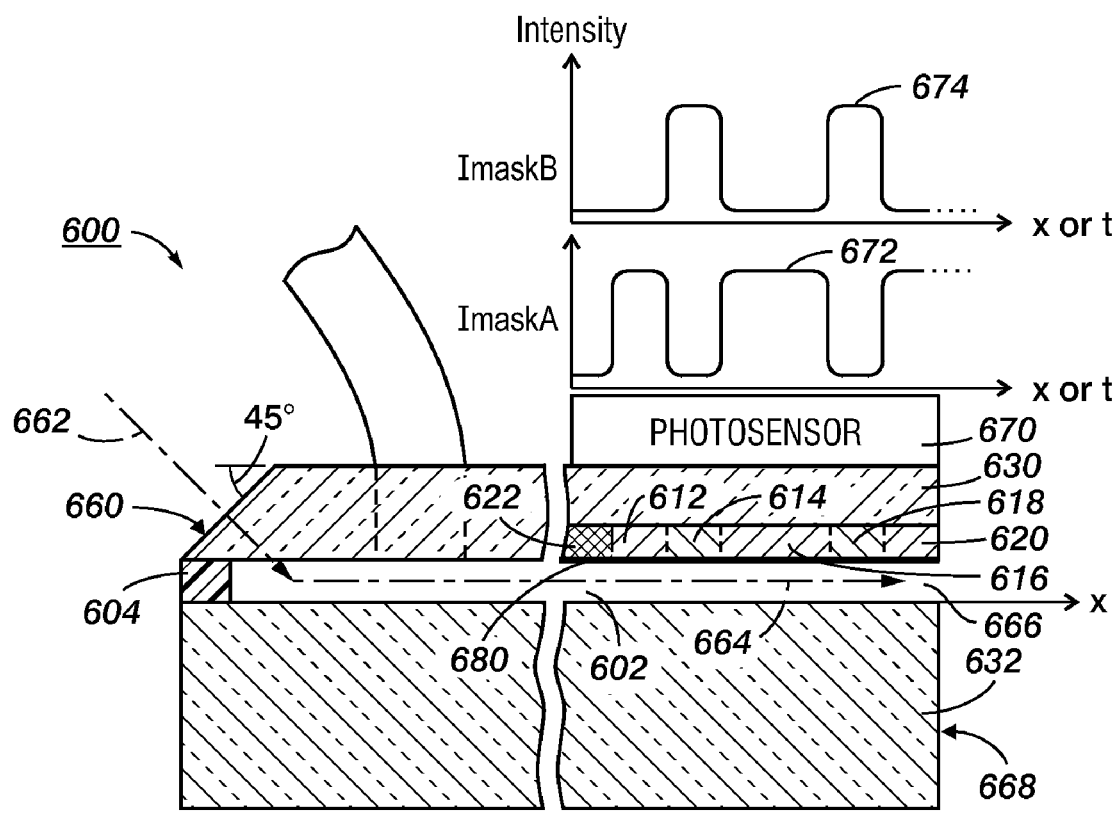
FIG. 7 is a cross-sectional view of another implementation of an article similar to that in FIG. 5, taken along the line 7-7, together with graphs of sensed intensities.

The cross section in FIG. 7 further illustrates how component 630 has oblique surface 660, a light interface surface that is illustratively at an angle of approximately 45° to the inward-facing surfaces of components 630 and 632. As a result, incident excitation light at a direction approximately perpendicular to surface 660, as illustrated by arrow 662, can cause and couple with light propagating through channel portion 602, as illustrated by arrow 664, as described, for example, in co-pending U.S. application Ser. No. 11/777,712, entitled "Producing Fluidic Waveguides", incorporated herein by reference in its entirety. Excitation light could have any appropriate wavelength, such as 266 nm, for example. The distance from surface 660 to obtain appropriate homogeneity can be determined, as described, for example, in U.S. Patent Application Publication No. 2008/0013877, incorporated herein by reference; the distance can also be sufficient to allow integration of blocking material 622.

In the illustrated implementation, the end of channel portion 602 at right in FIG. 7 is open, providing an additional port 666 through which fluid can enter into or exit out of channel portion 602. Alternatively, article 600, instead of ending at transverse end-surface 668, could extend to another area with ports similar to ports 608, such as with a part symmetrical about the position of surface 668; in this case, fluid could flow through channel portion 602 between ports 608 and similar ports at the opposite end of channel portion 602.

In the implementation in FIG. 7, the filters within filter assembly 610 are shown in cross section, and, in this implementation, filters 610, 612, 614, 616, 618, and 620 do not overlap, but rather are adjacent to each other. They could, for example, be integrated into a recess in the lower surface of component 630 such that they are even with the surrounding surface of component 630 or they could be surrounded on all sides by a layer of shadow (light blocking) or transparent material of the same thickness; in either of these approaches, the filters could be implemented so that there is no step at the edges of assembly 610. The size of the gap, if any, between adjacent filters depends, for example, on the resolution of the technique used to produce the filters. If the filters are produced by printing two different light-absorbing materials that have different absorption spectra (in which case a surrounding layer of shadow or transparent material could also be printed around them), the registration and gaps between filters depend on the resolution of the printing technique used; examples of such techniques are described in U.S. Patent Application Publication No. 2007/0172969, entitled "Additive Printed Mask Process and Structures Produced Thereby", and in co-pending U.S. patent application Ser. No. 11/755,717, entitled "Surface Energy Control Methods for Color Filter Printing", each of which is incorporated herein by reference in its entirety. In general, however, the techniques described herein do not require highly precise positioning of filters—a small gap between filters should not significantly affect time-varying signals that result from an object traveling past such filters while it emanates light.

The upper part of FIG. 7 includes two graphs illustrating intensities that would be detected by photosensor 670 in response to two types of objects, one emanating light of color "A", the other emanating light of color "B", in the case where filter assembly 610 included only filters 612, 614, 616, 618, and 620. Filters 612, 616, and 620 have bands that allow light of color "A" to pass, while filters 614 and 618 have bands that allow light of color "B" to pass.

Curve 672 illustrates intensities indicated by sensing results from photosensor 670 if object 640 emanates light of color "A" as it travels along the path through channel portion 602. In other words, the emanating light's photon energy distribution matches the band for filters 612, 616, and 620 so that curve 672 is high along those filters but low along filters 614 and 618; its high value is indicated on the vertical axis as "ImaskA".

Curve 674, on the other hand, illustrates intensity indicated by sensing results from photosensor 670 when object 640 emanates light of color "B" as it travels along the path. In this case, the emanating light has a photon energy distribution that matches the band for filters 614 and 618 but not for filters 612, 616, and 620, so that curve 674 is at a high intensity along filters 614 and 618, "ImaskB", and at a low intensity elsewhere.

Curves 672 and 674 illustrate an example in which two different types of objects provide signals that are approximately complementary, except at the far left along blocking material 622 where both curves are at approximately zero intensity. In a simple implementation, for example, filters 612, 616, and 620 could be red band pass filters, filters 614 and 618 could be green band pass filters, each object could either be a red fluorescing particle or tag, i.e., emanating light of color "A", or a green fluorescing particle or tag, i.e., emanating light of color "B". As suggested, curves 672 and 674 could be plotted based on the x-direction position of object 640 or based on the t-position within the time varying output signal from photosensor 670, which could be provided continuously or by any suitable form of sampling, such as by periodic readout at an appropriate frequency. The high intensities of curves 672 and 674 would be reduced to the extent that blocking material 622 prevents light from reaching photosensor 670.

As a result, output signals from photosensor 670 can be used to distinguish types of objects, in this case to distinguish objects that emanate light of color "A" from objects that emanate light of color "B", and examples of techniques that distinguish types of objects in various ways are mentioned below in relation to exemplary implementations. In some examples, emanating light encoded by a filter assembly with stripes of random lengths can be analyzed by comparing a resulting time-varying signal with one or more templates or other signals to determine an object's type, displacement, and position to a high level of precision.

FIG. 7 also illustrates, however, stack-equivalent filter 680 in filter assembly 610, illustratively on the lower surface facing toward channel portion 602, though it could be in any other suitable position. Stack-equivalent filter 680 would modify intensity of light received by filters 612, 614, 616, 618, and 620, such as in ways described below in relation to exemplary implementations. Therefore, curves 672 and 674 would be modified by presence of filter 680, allowing spatial modulation of emanating light to provide additional information about object 640 as it passes filter assembly 610.

Figure 8:
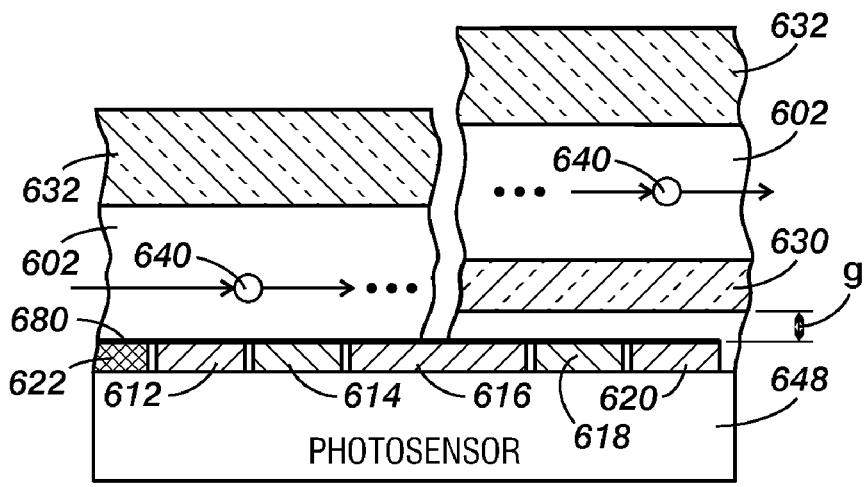
FIG. 8 is a partially schematic cross-sectional view showing two ways in which a filter arrangement on a photosensitive surface can be configured in an encoding component as in FIG. 2.

FIG. 8 illustrates two alternative implementations similar to those in FIGS. 5-7, and with the same reference numerals, but with filter assembly 610 on a photosensitive surface of photosensor 648. These implementations could be implemented by printing or otherwise depositing and patterning filters 612, 614, 616, 618, and 620 and blocking material 622, such as in the manner described above, or by producing a longitudinal sequence of band pass filters in any other appropriate way, with some possible techniques being described below in relation to other exemplary implementations. Then, possibly after preparation of an appropriate transparent layer over the other filters with a suitable surface for further microfabrication, filter 680 could be produced, such as in one of the ways described below in relation to exemplary implementations.

In the implementation at left in FIG. 8, photosensor 648 also operates as one side of channel portion 602, replacing light-transmissive component 630 along at least a portion of the channel. In other words, filter assembly 610 is positioned similarly to filter assembly 642 in FIG. 6, allowing a very small MFS. In the implementation at right in FIG. 8, photosensor 648 is outside of channel portion 602 separated from the outer surface of component 630 by a small gap of height g as shown. In this implementation, filter assembly 610 is positioned similarly to filter assembly 644 in FIG. 6, but not directly on the outer surface of component 630, so that a larger MFS is necessary. The gap between component 630 and photosensor 648 can be maintained by spacers or other appropriate support components, and can be sufficiently large that photosensor 648 does not interfere with anti-resonant waveguiding within channel portion 602, which can be implemented, for example, in the ways described in co-pending U.S. patent application Ser. No. 11/316,660, entitled "Providing Light to Channels or Portions", incorporated herein by reference in its entirety.

Absorption filters 612, 614, 616, 618, and 620 as described above in relation to FIG. 5-7 can be implemented in a multitude of ways. For example, rather than only two types of band pass filters that have bands for respective colors, three or more types of filters with three or more respective colors could be used. Similarly, a filter assembly can include band pass filters and other types of absorption filters as would be found in a shadow mask. Furthermore, with printed filters as described above or with other filters produced with layers of material, overlapping band pass filters could be produced, providing additional information. Other filter techniques are described in co-pending U.S. patent application Ser. No. 12/024,490, entitled "Transmitting/Reflecting Emanating Light with Time Variation", incorporated herein by reference.

Some of the exemplary implementations described below involve filter assemblies that combine periodic signals additively with template signals from filter sequences similar to some of those described above. The resulting time-varying signal emerges from the filter assembly with two different spatially varying patterns imposed on it. To produce such a signal, for example, a radial sequence or "stack" of filters similar to that shown in FIG. 3 could be used. Within a stack of filters, for example, one layer could be a template layer with an appropriate pattern to produce the template signal, while another layer could be a periodic layer with an appropriate pattern to produce the periodic signal; each of the template layer and periodic layer could have rectangles or other closed polygons of zero opacity surrounded by regions with opacity 0.5.

Figure 9:
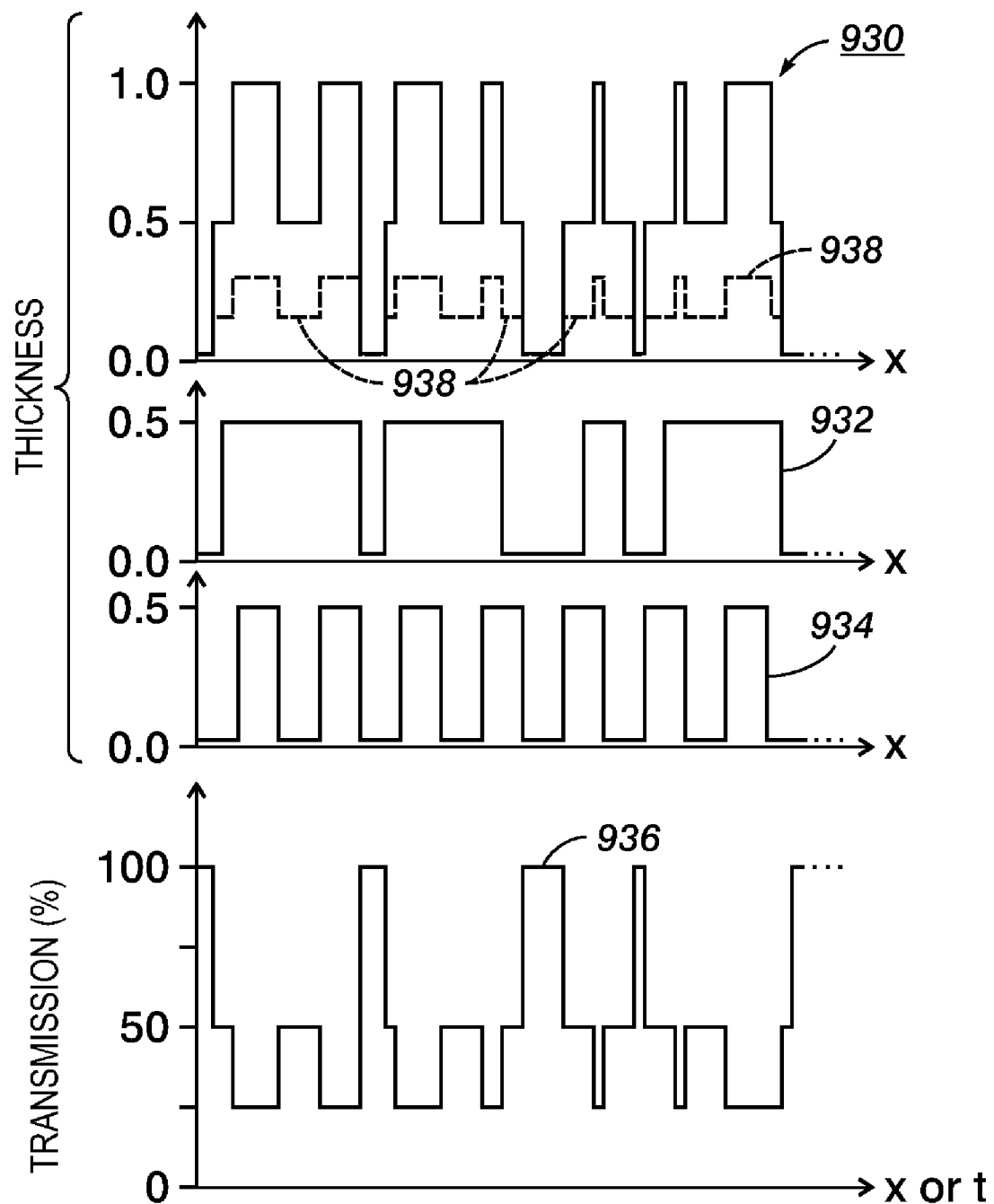
FIG. 9 includes a set of graphs showing cross-sectional thickness as a function of position in an x-direction for filters that can be implemented as in FIG. 1, showing transmission as a function of position in the x-direction or as a function of time t for one of the filters.
Figure 10:
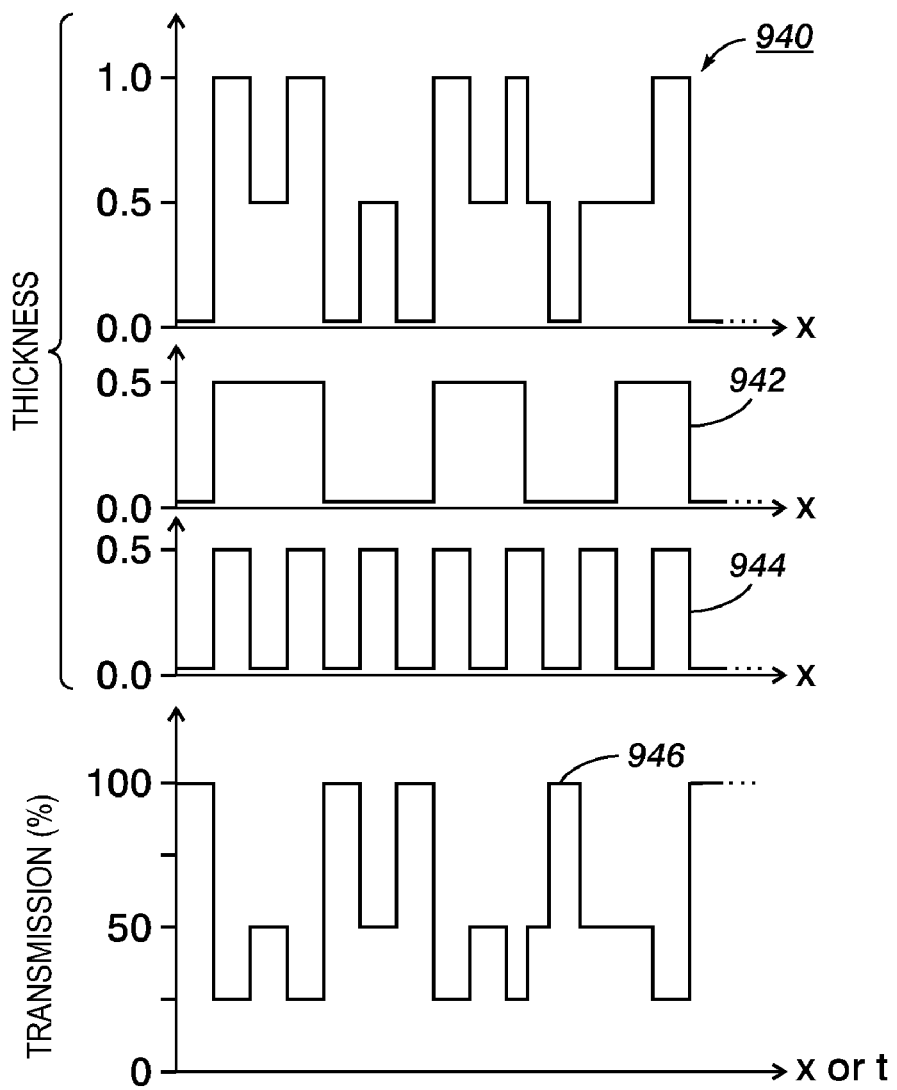
FIG. 10 includes a set of graphs showing cross-sectional thickness as a function of position in an x-direction for other filters that can be implemented as in FIG. 1, showing transmission as a function of position in the x-direction or as a function of time t for one of the filters.

FIGS. 9 and 10 illustrate an alternative approach that can be used with reflective gray level filters, producing a single filter assembly equivalent to a desired radial sequence or stack of filters. To obtain filters as in FIGS. 9 and 10, transmission functions, in this case thickness definitions, of two filter layers can be overlaid using software tools and the thicknesses of overlapping regions can be added to perform superposition, resulting in regions with thicknesses of 0, 0.5, and 1 in the example given above; the two filter layers could both be oriented with variation in the same direction, sometimes referred to herein as a transmission function's "variation direction", as in FIGS. 9 and 10, similar to the techniques of FIG. 5, or could be oriented with variation in different directions, e.g. orthogonal to each other. In any case, alignment and other orientation of such a filter assembly relative to an object path's longitudinal direction can affect encoding resolution, and the filter assembly might have a preferred orientation for optimal encoding. For implementations in which layer thickness does not appropriately define or determine the desired equivalent filter's structure or its optical variation, the techniques in FIGS. 9 and 10 could be modified to first overlay transmission functions such as optical feature definitions of the filters in which regions have defined optical feature values that determine the desired variation, thus obtaining a combined transmission function that is an optical feature definition of the desired equivalent filter obtained by superposition; the optical feature definition could then be converted to a layout-type description of the equivalent filter that is a combined transmission function in which each region has a defined optical thickness or other characteristic that can be produced to provide the region's value for the optical feature.

The techniques of FIGS. 9-10 take advantage of the fact that, in general, superpositions of filters are commutative, in the sense that the resulting transmission or reflection function is the same regardless of the order in which filters are superimposed. There are, of course, exceptions, such as where interference effects can occur if filters are in a specific order, or where alignment or other relationship of filter features can result in loss of different information depending on the order of the filters. These problems can in general be avoided by appropriately positioning simpler non-uniform transmission functions relative to each other before they are superimposed, such as in one of the ways described herein.

If the equivalent filter's transmission function is a thickness definition to produce a purely transmissive/reflective filter with no color variation, and if partial etching can be performed, an equivalent filter that approximates the equivalent filter definition can be constructed by first depositing a highly reflective material, such as chromium, over the entire filter assembly, and by then partially etching the reflective material away in regions with thickness 0 or 0.5 to an appropriate extent, leaving a thin, partially transmitting layer, after which the remaining reflective material can be etched away in regions with thickness of 0. Where partial etching is unreliable, other techniques may be used, such as by techniques that deposit a first patterned layer of thickness 0.5 with any suitable patterning technique, then depositing over it a second patterned layer of thickness 0.5 that is patterned without etching, such as with liftoff or other patterning techniques that do not require etching. Furthermore, similar techniques might be applied to produce layered filter structures that include DBRs of varying transmission/reflectivity and/or cavities of varying optical thickness, such as those described in co-pending U.S. patent application Ser. No. 12/024,490, incorporated above by reference; variation in cavity thickness could result from any appropriate combination of thickness variation and refractive index variation, produced with any appropriate techniques.

Filter 930 in FIG. 9 is equivalent to the combination of a random filter and a periodic filter, superimposed one on the other. Curve 932 shows the shape of the random filter, while curve 934 shows the shape of the periodic filter; as can be seen, the random and periodic filters both have only two thickness levels, either 0 or 0.5, but filter assembly 930 has three thickness levels, corresponding to 0, 0.5, and 1. Curve 936 shows a resulting transmission function. Emanating light passing through filter assembly 930 includes both displacement and position information about an object from which it emanates, and allows time-scaling techniques to extract that information, as described below.

The technique illustrated in FIG. 9 can be adjusted as suggested by dashed lines 938 within filter 930. In other words, total light output can be changed by scaling the amplitude of the thickness levels: rather than 0, 0.5, and 1, for example, thickness levels of 0, 0.2, and 0.4 could be used, allowing greater light transmission. It may be necessary, however, to make a tradeoff between greater light output, and therefore total signal intensity, on the one hand, and greater light modulation on the other—greater light modulation may facilitate calculation of displacement and position within a given observation region. The mask suggested by dashed lines 938 emphasizes total light output because it has reduced thickness and, conversely, increased transmission, with a thickness of 0 being equivalent to transmission of 1 and vice versa. The scaling suggested by dashed lines 938 may require great precision: the x-direction scale of features in assembly 900 may be as great as 10 µm, while a useful thickness may be as thin as 10 nm of chromium.

Similarly, filter assembly 940 in FIG. 10 is equivalent to the combination of a chirp filter represented by curve 942 and a periodic filter represented by curve 944. A combination of chirp and periodic filters can make it possible to more efficiently extract displacement and position information about objects that may have different speeds. Curve 946 shows a resulting transmission function, which allows information extraction.

A stack-equivalent filter assembly as in FIGS. 9 and 10 can in some cases have a smaller MFS than either of the simpler non-uniform filters. As mentioned above, loss of resolution can occur for light emanating from objects approximately as large as the MFS. In such cases, it may be advantageous to change alignment or other relative orientation of the simpler filter's transmission functions in producing the stack-equivalent filters, such as in one of the ways described below in relation to production of stack-equivalent filters.

Figure 11:
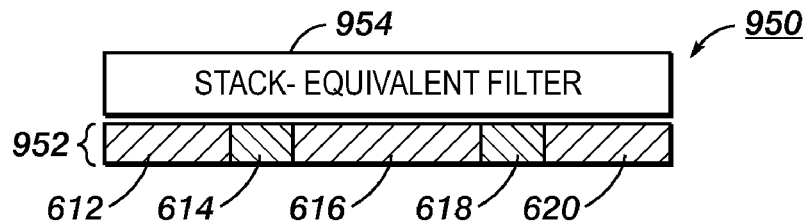
FIG. 11 is a schematic cross-sectional view of a filter assembly that includes two filters, one a stack-equivalent filter that can be implemented as in FIG. 1.

FIG. 11 illustrates one way in which a longitudinal sequence of filters, such as a random band pass filter arrangement as described above in relation to FIGS. 5-7 can be combined with a stack-equivalent filter such as a reflective gray level filter arrangement, e.g. with any suitable combination of periodic, random, and/or chirped transmission functions. Filter arrangement 950 in FIG. 11 includes filter subassembly 952 with a longitudinal sequence similar to that described above in relation to FIGS. 5-7. On the upper surface of subassembly 952 is stack-equivalent filter 954, within which, for example, different positions could have respective intermediate transmission levels such as 0.3, 0.5, or 0.6. As a result, filter assembly 950 implements stack equivalent filter 680 (FIGS. 7-8) with techniques similar to those of FIGS. 9-10, providing distinguishable time-varying signals for emanating light of different colors, and also modulating the emanating light to allow various other information extraction techniques, such as those described in co-pending U.S. patent application Ser. Nos. 12/022,485, entitled "Obtaining Information From Time Variation of Sensing Results", and 12/024,490, entitled "Transmitting/Reflecting Emanating Light with Time Variation", both incorporated herein by reference. For example, time-scaling operations can be performed in the same way for each emanating color's signal, and the different color signals can be used to distinguish types of objects after time scaling.

Figure 12:
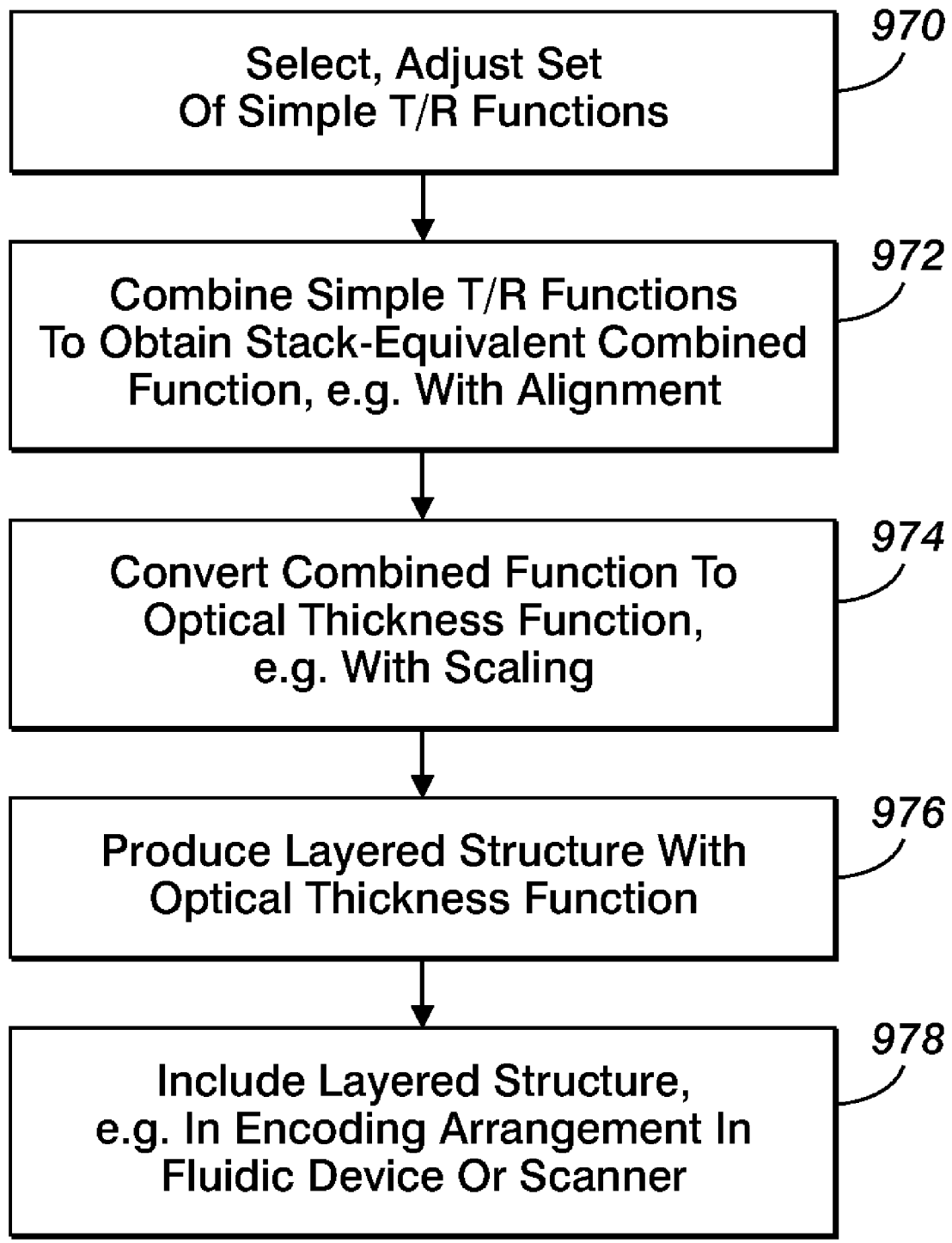
FIG. 12 is a flow chart showing operations in a way of producing filters such as those in FIGS. 9-11.

FIG. 12 illustrates exemplary operations in producing articles with stack-equivalent filters like those described above in relation to FIGS. 5-11. In particular, the operations in FIG. 12 make it possible to produce filter assemblies that can be used, e.g. in flow cytometry or gray level or multicolor scanners, to transmit/reflect light emanating from moving objects with time variation. The emanating light can then be photosensed and the sensing results used to obtain information about the moving objects, such as their positions, speeds, and spectra. In general, each operation in FIG. 12 could be implemented with any appropriate combination of manual and automatic operations, including any suitable user interface techniques for selecting or controlling operations.

The operation in box 970 in FIG. 12 obtains a set of simple T/R functions. This operation can include selecting two or more T/R functions and then adjusting each of them. The T/R functions could be one-dimensional optical thickness functions like those in curves 932, 934, 942, and 944 in FIGS. 9 and 10, two-dimensional optical thickness functions, or one- or two-dimensional functions of any other appropriate optical feature, such as spectrum across an application's range of photon energies. Among possible adjustments include clipping or otherwise modifying the scale or resolution of a T/R function. Scaling could be especially important for signal separation into discrete wavelength bands, because spatial frequencies in a T/R function would have counterpart time frequencies in emanating light; in this and other situations, fourier transforms or other such transforms of the simple T/R functions could be compared to obtain information necessary to perform appropriate scaling or other adjustments.

The operation in box 972 then combines the simple T/R functions from box 970 to obtain a stack-equivalent combined T/R function. The simple T/R functions can be combined in any suitable way, depending on the optical feature involved. For example, for optical thickness functions as in curves 932, 934, 942, and 944 (FIGS. 9 and 10), a combining operation such as addition or multiplication may be appropriate, with curves 930 and 940 illustrating addition; in other contexts, subtraction or division might be appropriate, or another combining operation related to one or more of the above, such as taking an arithmetic or geometric mean. Also, in combining more than two functions, each combining operation can be pairwise, with results similarly be combined in a pairwise manner, a mean or other such combining operation can be performed over all the functions at once, or any combination of these and other approaches.

The operation in box 972 can also include, before the combining operation, any appropriate aligning or other orientation adjustment of the simple T/R functions. If the simple T/R functions are one-dimensional as in FIGS. 9 and 10, they can be shifted as desired, such as to avoid situations where transitions coincide or where MFS is too small for a given application, but also to ensure that the combined transmission function will provide output light with time variation in accordance with all of them. If they are two-dimensional, they can similarly be shifted in the second dimension and/or rotated relative to each other, such as to produce a stack-equivalent filter with orthogonal periodic T/R functions, which might be useful in obtain speed information in each of two orthogonal directions, possibly with different frequencies for signal separation. The operation in box 972 might be based on an assumed set of object paths relative to the combined transmission function, such as in a range of directions, and appropriate information about these paths can be saved for subsequent use.

The operation in box 974 converts the combined T/R function from box 972 to a counterpart optical thickness function. This conversion can be performed as appropriate for a desired type of filtering, whether transmissive (as in FIGS. 9 and 10), reflective, interference-based, or other filtering is desired. For transmissive and/or reflective gray level filtering, techniques as in FIGS. 9 and 10 may obtain satisfactory thickness functions. For transmissive/reflective color filtering, however, it may be necessary to include information in the combined T/R function about the desired spectrum in each region of the equivalent filter, which could result in a much more complex data structure than would be necessary solely for intensity filtering. For interference-based filtering, on the other hand, optical thickness determines transmitted photon energy (i.e. wavelength or frequency), so that it determines color, and intensity variations might be obtained by adjusting parameters other than optical thickness. A raw optical thickness function for a transmissive/reflective filter could be scaled as suggested by dashed lines 938 (FIG. 9) to obtain desired intensity levels.

The operation in box 976 then produces a layered structure having the optical thickness function from box 974. As implied above in relation to FIGS. 7, 8, and 11, the layered structure could be produced directly on another filter assembly such as a random multicolor filter, on a transparent layer over such a filter, or on any other suitable support surface with desired optical properties. Techniques as in FIGS. 6 and 8 could be modified to produce the layered structure directly on a photosensor's photosensitive surface, which might be advantageous both in fluidic implementations like flow cytometry but also in scanning implementations, such as on a CCD or CMOS photosensing chip that can be moved relative to documents or other images during scanning. In flow cytometry and other fluidic implementations, it may instead be advantageous to produce the layered structure directly on the inward-facing surface of a channel wall or other component bounding a channel. In some cases, the layered structure could be produced on an appropriate substrate, and the substrate with layered structure on it could then be mounted on or otherwise connected to other components.

As described above, partial etching techniques could be used if feasible, either alone or in combination with other techniques that do not require etching; if partial etching is not feasible, patterning techniques that do not require etching could be used, possibly including variations on liftoff, embossing, molding, and so forth, as appropriate for materials, dimensions, and tolerances involved in a given implementation. For layered filter structures that include DBRs of varying transmission/reflectivity and/or cavities of varying optical thickness, any appropriate combination of thickness variation and refractive index variation could be produced with any appropriate techniques. In some implementations, doping or other modifications of the layered structure could be performed to produce regions with desired spectra.

Finally, the operation in box 978 includes the layered structure from box 976, however produced, in whatever environment is appropriate for a given application, taking into account the information about object paths from box 972. For example, the layered structure could be included in an encoding arrangement that can then be used in a fluidic device, e.g. for flow cytometry, or in a scanning device, e.g. for copying and/or printing. A particularly interesting potential application is to hyperspectral image sensing in copying and printing applications. The operation in box 978 can also include making any electrical, optical, or fluidic connections necessary for operation of a resulting device, and also calibration or other preliminary operations necessary to obtain reference data for use in adjusting or otherwise modifying sensing results during operation.

The technique of FIG. 12 could be modified in many ways within the scope of the invention. For example, the operations in boxes 970, 972, and 974 could be combined in any appropriate way to obtain an optical thickness function from information about desired sensing results, possibly more directly than shown in FIG. 12. Furthermore, the technique of FIG. 12 is extremely general, and could be employed to produce a wide variety of filters, including numerous types of stack-equivalent filters.

Some techniques as described above have been successfully simulated. In particular, a simulated observed signal has been obtained that contains both an encoding based on a random template from a filter and also a periodic modulation from a superimposed filter. Resulting photosensed signals with additive noise have been processed, using time scaling to perform comparison, and where the observed signal has an unknown time scaling that occurs before it is observed; S/N ratio of 0.5 has been obtained and 0.1 appears achievable. These results could be obtained with particle speeds up to 0.5 m/sec and higher speeds up to a few m/sec appear to be feasible, with particles having effective sizes down to 0.6 µm, and with particle separations down to a given implementation's MFS. A demonstration included counting CD4 in a whole blood sample; single tag detection was shown to be feasible.

Where a simulated observed signal includes or is accompanied by a simulated concurrent periodically modulated signal, time scaling of a template waveform based on a scaling factor from the periodically modulated signal has successfully produced matching correlation results, indicating correlation or anti-correlation as appropriate and making spectral information available, in effect allowing concurrent detection of multiple colors with a single detector such as a large-area photosensor. Because an object receives different excitations at almost the same time and location (due, for example, to interdigitated or otherwise patchworked or patterned excitations), differences in absorption and excitation spectra can be measured with very high precision; similarly, because different spectral subranges of an object's emission spectra are measured at almost the same time and location (due, for example, to interdigitated, or otherwise patchworked or patterned filter arrangements), differences in emission spectra can be measured with very high precision; therefore, with one or both of patterned excitation and patterned filtering, many types of errors cancel out, including time-dependent factors such as bleaching, intermixing, diffusion and also errors induced by excitation differences such as temperature gradients and optical misalignments. Particle position can be precisely determined from fine structure of correlation results. As noted above, simulation results show that spatial resolution of less than 1.0 µm is possible, and single fluorescence markers can be detected, making detection possible with smaller amounts of consumables such as markers. The techniques appear appropriate for native fluorescence, allowing agent-less detection.

The use of filters with combined transmission functions from superposition or scaled superposition as described herein allows concurrent encoding of more than one type of information about an object, e.g. speed and spectra or speed and phase. Filters with combined transmission functions could be produced in very thin layered structures on surfaces inside or outside a fluidic channel, such as in a flow cytometer, and scaling could be used to obtain desired output light intensity. It is expected that high spatial resolution will be achievable with precise fabrication techniques. A wide variety of masks and other optical filters could be produced with such techniques.

Implementations as described above in relation to FIGS. 1-12 could be advantageously applied in a wide variety of sensing applications, possibly including, for example, fluorescence- or impedance-based flow cytometry or other biodetector applications that seek a signature of a particle of unknown velocity; such biodetectors often use microfluidic channels with inhomogeneous flow profiles, causing variation in particle velocity. The techniques can be used to count or obtain ratios between fluorescing objects of different types, such as different types of tagged cells, particles, tagged DNA, and so forth. In such an application, calibration can be performed using known objects, e.g., tagged beads, with known velocities to obtain template waveforms that include deviations caused by fabrication tolerances but can then be compared with sensed waveforms to obtain information about unknown objects. To improve S/N, known and sensed waveforms can be correlated, such as after time scaling of each known waveform. If a sensed waveform includes or is accompanied by periodic modulation, a periodicity value such as a frequency can be used to obtain a scaling factor for time scaling before correlation, allowing more rapid correlation than if a brute force technique is used to find a satisfactory time scaling.

Implementations described above may be advantageous in biodetector applications that require compact, low-cost components without critical optics and with high sensing efficiency. Such applications might include point-of-care flow cytometry (such as with an integrated flow cytometer), DNA analysis, proteomics, and so forth.

Implementations described above could successfully detect native fluorescence differences between biological materials. Most biological cells are composed of only a few basic building blocks and, therefore, exhibit similar native fluorescence spectra. Interdigitated or otherwise patch-worked or patterned filter arrangements like those above are particular suitable for differentiation of objects based on their native fluorescence signals because the techniques are sensitive enough to detect the native fluorescence from a single cell and allow direct measurement of distinguishing features such as intensity ratios in emission spectra. In addition, implementations of the techniques can combine advantages of excitation and emission spectroscopy in a rugged and compact system.

Also, implementations described above could be applied in scanning of bio-chips or documents where objects have different emanation spectra, and so forth. The techniques may also be applicable in various low S/N ratio systems in which a known signal is bounced off an object traveling at an unknown velocity, such as where object velocity is on the order of signal propagation velocity, as in SONAR. The techniques may be especially advantageous where precise information about position, speed, or type of objects is sought.

Exemplary implementations described above employ photosensors or impedance-based sensors with specific features, but a wide variety of sensors could be used to obtain sensing results indicating values of various parameters other than emanating light intensity, parameters that can have time variation that indicates information about objects. Similarly, implementations described above involve sensing information about objects that are moving in fluidic channels or that are moving relative to a sensor such as in scanning, but various other types of fluidic implementations or other implementations in which objects move in various other ways could be sensed to obtain sensing results suitable for techniques described above. For example, information could be obtained from native fluorescence of particles in an air stream. Also, an excitation pattern could be scanned across a glass slide with immobilized analyte particles such as tagged cells or DNA spots, to obtain emanating fluorescent light.

Components of exemplary implementations as described above could have various shapes, dimensions, or other numerical or qualitative characteristics other than those illustrated and described above. For example, a wide variety of different simpler non-uniform transmission functions besides those mentioned could be positioned or oriented relative to each other in any of various ways and then superimposed in any of various ways to obtain combined transmission functions on which various types of scaling could then be performed. Also, the resulting combined transmission function could then be implemented in a multitude of different filters, including various types of absorbing, transmitting, reflecting, and interference-based filters, with transmission functions that can include binary, gray level, and/or color features. The above exemplary implementations generally involve superposition of two functions, but three or more functions could in principal be superimposed, provided it is possible to find an appropriate relative positioning that allows concurrent encoding by all the functions. Similarly, although the exemplary implementations generally involve sensing from a single fluidic channel, implementations could readily include multiple parallel channels, allowing parallel sensing and readout and larger scale sensing.

Some of the above exemplary implementations involve specific types of fluidic components, filter components, light source components, displacement control components, sensors, and so forth, but the invention could be implemented with a wide variety of other types of components. For example, some implementations use specific types of spatial modulation based on one or more of an excitation pattern, a filter assembly, and/or displacement control, but various other types of spatial modulation could be used, including any appropriate combination of color, gray level, and black and white patterning and including other patterning techniques such as patterned sensing; for example, in a fluidic implementation, a filter assembly or a patterned photosensor could be printed or otherwise produced on an inward wall or other boundary of a channel or in another appropriate location. Also, some exemplary implementations use specific types of processing, such as digital signals obtained after converting sensed analog values. In general, however, the invention could be implemented with any suitable signal processing techniques, including any appropriate combination of analog and digital processing; either or both of two compared waveforms could be obtained in analog or digital form, and any combination of time scaling could be performed before comparison. Further, some exemplary implementations use large area photosensors, but various ICs with photosensing arrays might be used.

Some of the above exemplary implementations involve specific types of emanating light, e.g. fluorescence, and specific types of excitation and filtering suitable to fluorescent light, but these are merely exemplary. The invention could be implemented in relation to various other types of optical signals in various other ranges of photon energies or with any other appropriate sensed stimuli.

Some of the above exemplary implementations involve specific materials, such as in fluidic structures with light-transmissive components or in filtering arrangements with reflective material such as chromium or light blocking material such as amorphous silicon, but the invention could be implemented with a wide variety of materials and with layered structures with various combinations of sublayers. Thicknesses of layers may vary across any suitable range.

An exemplary implementation could employ a CPU, which could be a microprocessor or any other appropriate component. Furthermore, as noted above, operations could be performed digitally or with analog signals, and could be done either on the same IC as a photosensor array, on other components, or on a combination of the two, with any appropriate combination of software or hardware.

The above exemplary implementations generally involve use of encoding/sensing arrangements, sensors, photosensors, excitation arrangements, filter arrangements, displacement control arrangements, and so forth following particular operations, but different operations could be performed, the order of the operations could be modified, and additional operations could be added within the scope of the invention.

For example, readout of sensed quantities from a sensor to obtain a sensed time-varying waveform could be performed serially or in parallel, and, with an array, could be performed cell-by-cell or in a streaming operation. Principal component analysis could be applied to specifically chosen intensity ratios in the emission spectrum in distinguishing cells or other objects, possibly allowing identification. Multiple photosensors along a channel could measure different intensity ratios in the emission spectrum, possibly allowing identification of objects based on either emission characteristics. Dyes that are very similar may be distinguishable if they reveal only slightly different emission spectra, and use of similar dyes could be advantageous in satisfying pH requirements within cytometers.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. An article of manufacture comprising:
    a transmissive/reflective filter with a combined transmission function within an application's range of photon energies, the combined transmission function being approximately equal to a superposition or scaled superposition of a set of simpler transmission functions, the set including two or more simpler non-uniform transmission functions; in the superposition or scaled superposition, each of a subset of at least two of the simpler non-uniform transmission functions being different from each other and positioned relative to each other so that, in response to input light within the application's range of photon energies emanating from objects traveling along any of one or more paths past the filter, the filter provides output light with time variation in accordance with each of the functions in the subset.

2. The article of claim 1 in which the filter is structured to do at least one of:
    transmit the input light to provide the output light; and
    reflect the input light to provide the output light.

3. The article of claim 1 in which each of the functions in the subset is one of:
    a periodic function;
    a random function; and
    a chirp function.

4. The article of claim 3 in which the subset includes a random function and a periodic function.

5. The article of claim 3 in which the subset includes a chirp function and a periodic function.

6. The article of claim 1 in which each of the functions in the subset varies along a respective variation direction; the functions in the subset being positioned so that their variation directions are parallel.

7. The article of claim 6 in which the functions in the subset are one-dimensional functions.

8. The article of claim 1 in which the filter's optical thickness varies as a function of position; the combined transmission function depending on the optical thickness.

9. The article of claim 8 in which the filter is a layered structure, the filter's optical thickness depending on at least one of:
    thickness of one or more layers in the layered structure; and
    refractive index of one or more layers in the layered structure.

10. The article of claim 1 in which the article further comprises:
a detector, the detector including:
a photosensor with a photosensitive surface; and
a filter assembly on the photosensitive surface of the photosensor, the filter assembly including the transmissive/reflective filter.

11. The article of claim 10 in which the filter assembly further includes:
a transmissive multicolor filter between the photosensitive surface and the filter.

12. The article of claim 10 in which the article is one of:
a flow cytometer; and
a scanner.

13. Apparatus that can be operated in an application, the apparatus comprising:
a fluidic structure that includes a channel through which objects can travel along respective paths during operation of the apparatus; and
an encoding component; the encoding component including a filter assembly that can receive light emanating from objects in the channel; in response to input light that is within the application's range of photon energies and that is emanating from an object traveling through the channel past the filter arrangement, the filter assembly providing output light; the filter assembly including:
a filter element with a combined transmission function within the application's range of photon energies, the combined transmission function being approximately equal to a superposition or scaled superposition of a set of two or more simpler transmission functions, the set including two or more simpler non-uniform transmission functions; in the superposition or scaled superposition, each of a subset of at least two of the simpler non-uniform transmission functions being different from each other and positioned relative to each other so that, in response to the input light, the filter assembly provides the output light with time variation in accordance with each of the functions in the subset.

14. The apparatus of claim 13 in which the apparatus is a flow cytometer; the objects being biological cells or viruses.

15. The apparatus of claim 14 in which the objects have emission cones on an input surface of the filter element, the combined transmission function having a minimum feature size approximately as large as or larger than the emission cones.

16. The apparatus of claim 13 in which the filter assembly is one of:
on an inside surface of a part bounding the channel;
on an outside surface of a part bounding the channel;
spaced by a gap from an outside surface of a part bounding the channel; and
positioned outside the channel so that an optical element outside the channel images the input light onto the filter assembly.

17. A method of using a fluidic structure that includes a channel in an application in which objects travel through the channel, the method comprising:
while each of a series of one or more objects emanates respective light within the application's range of photon energies as it travels along a respective path through the channel, transmitting/reflecting a portion of the object's respective light through a filter component along the channel to provide output light; the act of transmitting/reflecting a portion of the light including:
transmitting/reflecting the portion of the light in accordance with a combined transmission function within the application's range of photon energies, the combined transmission function being approximately equal to a superposition or scaled superposition of a set of two or more simpler transmission functions, the set including two or more simpler non-uniform transmission functions; the filter component being positioned relative to the channel and each of a subset of at least two of the simpler non-uniform transmission functions being different from each other and positioned relative to each other in the superposition or scaled superposition so that, in response to the portion of the light, the output light has time variation in accordance with each of the functions in the subset.

18. The method of claim 17 in which the act of transmitting/reflecting further comprises:
transmitting the output light through a random multicolor filter so that the output light further has time variation in accordance with the random multicolor filter.

19. A method comprising:
producing a filter that transmits/reflects light within an application's range of photon energies; the act of producing the filter including:
producing the filter with a combined transmission function within the application's range of photon energies, the combined transmission function being approximately equal to a superposition or scaled superposition of a set of two or more simpler transmission functions, the set including two or more simpler non-uniform transmission functions; in the superposition or scaled superposition, each of a subset of at least two of the simpler non-uniform transmission functions being different from each other and positioned relative to each other so that, in response to input light within the application's range of photon energies emanating from objects traveling along any of one or more paths past the filter, the filter provides output light with time variation in accordance with each of the functions in the subset.

20. The method of claim 19, further comprising:
mathematically combining the functions in the subset.

21. The method of claim 20 in which each of the functions in the subset has a respective variation direction; the method further comprising, before the act of mathematically combining the functions, at least one of:
positioning the functions in the subset so that their variation directions are approximately parallel; and
positioning the functions in the subset to adjust the combined transmission function's minimum feature size.

22. The method of claim 20 in which the act of producing the filter with the combined transmission function includes:
converting the mathematically combined functions in the subset to an optical thickness function; and
using the optical thickness function in producing the filter.

23. The method of claim 22 in which the act of using the optical thickness function includes:
scaling the optical thickness function to obtain a scaled optical thickness function; and
producing the filter so that it has the scaled optical thickness function.

24. The method of claim 19 in which the filter has a range of path directions in which output light has time variation, the method further comprising:
connecting the filter into a device so that objects move past the filter along paths within the range of path directions.

* * * * *